United States Patent
Laddha et al.

(10) Patent No.: US 10,463,707 B2
(45) Date of Patent: Nov. 5, 2019

(54) PROCESS FOR PREPARING HERBAL EXTRACTS

(71) Applicant: MOLEAC PTE LTD., Helios (SG)

(72) Inventors: Kirti S Laddha, Mumbai (IN); Shreeram N. Agharkar, Princeton, NJ (US)

(73) Assignee: MOLEAC PTE LTD., Helios (SG)

( * ) Notice: Subject to any disclaimer, the term of this patent is extended or adjusted under 35 U.S.C. 154(b) by 0 days.

(21) Appl. No.: 15/759,645

(22) PCT Filed: Sep. 13, 2016

(86) PCT No.: PCT/SG2016/050444
§ 371 (c)(1),
(2) Date: Aug. 9, 2018

(87) PCT Pub. No.: WO2017/048191
PCT Pub. Date: Mar. 23, 2017

(65) Prior Publication Data
US 2018/0264062 A1  Sep. 20, 2018

(30) Foreign Application Priority Data
Sep. 14, 2015 (SG) .......................... 10201507607R

(51) Int. Cl.
| | |
|---|---|
| *A61K 36/00* | (2006.01) |
| *A61K 36/481* | (2006.01) |
| *A61K 36/882* | (2006.01) |
| *A61K 36/232* | (2006.01) |
| *A61K 36/236* | (2006.01) |
| *A61K 36/286* | (2006.01) |
| *A61K 36/537* | (2006.01) |
| *A61K 36/65* | (2006.01) |
| *A61K 36/69* | (2006.01) |
| *A61K 36/736* | (2006.01) |
| *A61K 36/888* | (2006.01) |
| *B01D 11/02* | (2006.01) |

(52) U.S. Cl.
CPC .......... *A61K 36/481* (2013.01); *A61K 36/232* (2013.01); *A61K 36/236* (2013.01); *A61K 36/286* (2013.01); *A61K 36/537* (2013.01); *A61K 36/65* (2013.01); *A61K 36/69* (2013.01); *A61K 36/736* (2013.01); *A61K 36/882* (2013.01); *A61K 36/888* (2013.01); *A61K 2236/00* (2013.01); *A61K 2236/33* (2013.01); *A61K 2236/51* (2013.01); *A61K 2300/00* (2013.01); *B01D 11/02* (2013.01)

(58) Field of Classification Search
None
See application file for complete search history.

(56) References Cited

FOREIGN PATENT DOCUMENTS

| | | | |
|---|---|---|---|
| CN | 1657084 | A | 8/2005 |
| CN | 1709486 | A | 12/2005 |
| CN | 1951482 | A | 4/2007 |
| CN | 1965966 | A | 5/2007 |
| CN | 101244208 | A | 8/2008 |
| CN | 102078520 | B | 7/2012 |
| CN | 102600321 | A | 7/2012 |
| CN | 102886026 | A * | 1/2013 |
| CN | 103705845 | A | 4/2014 |
| CN | 102847061 | B | 5/2014 |
| CN | 102846824 | B | 7/2014 |
| CN | 104225417 | A | 12/2014 |
| CN | 104258040 | A | 1/2015 |
| CN | 104383464 | A | 3/2015 |
| CN | 103947888 | B | 9/2015 |
| EP | 1930020 | A1 | 6/2008 |
| KR | 2006117550 | A * | 5/2005 |
| WO | WO 2007/106049 | A1 | 9/2007 |
| WO | WO 2010/053456 | A1 | 5/2010 |
| WO | WO 2010/110755 | A1 | 9/2010 |
| WO | WO 2013/141818 | A1 | 9/2013 |

OTHER PUBLICATIONS

Extended European Search Report for European Application No. 16846968.2, dated Apr. 3, 2019, 9 pages.
International Search Report dated May 12, 2016, by the International Searching Authority for Application No. PCT/SG2016/050444, filed Sep. 13, 2016, 7 pages.

* cited by examiner

*Primary Examiner* — Qiuwen Mi
(74) *Attorney, Agent, or Firm* — Cooley LLP

(57) ABSTRACT

The present invention relates to a process for preparing pharmaceutical compositions and other herbal products derived from herbs of Traditional Chinese Medicine (TCM), including *Radix astragali* (Milkvetch—Huang Qi), *Ligusticum chuanxiong* (Chuan Xiong), *Radix angelicae sinensis* (Chinese *Angelica*—Dang Gui) and *Radix polygalae* (Thinleaf milkwort—Yuan Zhi). The process includes a single extraction of the TCM herbs by heating in a hydro-alcoholic solvent, wherein the alcohol may be ethanol. FIG. 2 provides an overview of one embodiment of the process. The invention also relates to products of the process of the invention, and their use in the treatment of stroke and various neurological disorders.

29 Claims, 3 Drawing Sheets

PROCESS FOR PREPARING HERBAL EXTRACTS

CROSS-REFERENCE TO RELATED APPLICATIONS

This application is the U.S. national stage application to International Patent Application No. PCT/SG2016/050444, filed on Sep. 13, 2016, which claims the benefit of priority to Singapore Patent Application No. 10201507607R, filed on Sep. 14, 2015, the contents of which are incorporated herein by reference in their entireties.

FIELD OF THE INVENTION

The present invention relates to a new process for preparing herbal extracts used in Traditional Chinese Medicine (TCM). The invention also relates to new products obtainable by the process described herein, as well as to uses of the same, such as in the treatment of stroke and various neurological disorders.

BACKGROUND

The present invention is concerned with a new, simplified process for the concomitant production of certain herbal extracts, and to new products obtainable by the process. The process of the invention includes a novel extraction step with the resulting extracts having use in the preparation of herbal products having medicinal benefits.

The present invention may, in particular, be applied to the production of multiple extracts used in the preparation of the commercial products MLC601™ and MLC901™. MLC601™ and MLC901™ are TCMs comprising nine TCM herbal extracts. MLC601™ and MLC901™ are primarily used in the treatment of cerebral stroke, but various other uses have been reported, including uses described in WO2007/106049, WO2010/053456, WO2010/110755 and WO 2013/141818, the contents of which are incorporated herein by reference.

CN 1965966A describes a process for producing MLC601, comprising the nine herbal TCM extracts of MLC901 in addition to five TCM extracts of animal origin. The process includes a water extraction step which consists of boiling in water nine herbal TCMs three times for 1 to 4 hours each time. The resulting extracts are further processed by concentration, alcohol precipitation, ethanol recovery and drying steps to produce a paste. The five animal TCM extracts are then added, the paste ground into a powder and formed into granules, which are sprayed with volatile oils from *Rhizoma Chuanxiong, Angelica* and *Acorus gramineus*, and packing into capsules.

The present process has major, multiple and non-obvious modifications over prior processes to provide herbal TCM extracts which may be incorporated into products such as MLC601 and MLC901.

SUMMARY

In accordance with the present invention, there is provided a process for preparing herbal extracts which comprises heating a mixture of the following herbs:
(i) *Radix Astragali* (root of Membranous Milkvetch or Huang Qi);
(ii) Rhizome of *Ligusticum Chuanxiong* (Chuan Xiong);
(iii) *Radix Angelicae sinensis* (root of Chinese *Angelica* or DanGui); and
(iv) *Radix Polygalae* (root of thinleaf milkwort, *Polygala tenuifolia Willd., Polygala sibirica* L. or Yuanzhi)
in an aqueous organic solvent, to produce a solution containing the herbal extracts.

The process may also optionally include the extraction of one or more additional herbs selected from:
a) *Radix et Rhizoma Salviae Miltiorrhizae* (Red Sage root or Dan Shen);
b) *Radix Paeoniae rubra* (Red Peony root):
c) Flower of *Carthamus Tinctorius* (Safflower or HongHua);
d) *Semen Persicae* (*Prunus Persica* seeds or Taoren); and
e) *Rhizoma Acori tatarinowii* (rhizome of grassleaf sweetflag or Shichangpu).

The process of the present invention enables improved manufacturing capability due to its enhanced simplicity, convenience and effectiveness. In particular, the process requires fewer steps than in prior reported processes, and various time-consuming steps may be omitted. The resulting benefits include reductions in processing time, energy and cost.

The process of the present invention may be used to prepare the products MLC 601 or MLC901 without the inclusion of a step involving the removal and use of volatile oil from *Rhizoma Chuanxiong, Angelica* and *Acorus gramineus*. The process also does not require alcohol precipitation or multiple extractions on the same mass, as is reported in prior processes for preparing MLC 601 and MLC901. Indeed, the process of the present invention may conveniently comprise a single extraction step.

The present invention also demonstrates increased process reproducibility, leading to more consistent batches of product when scaled up to production levels.

Glossary

This section is intended to provide guidance on the interpretation of the words and phrases set forth below (and where appropriate grammatical variants thereof). Further guidance on the interpretation of certain words and phrases as used herein (and where appropriate grammatical variants thereof) may additionally be found in other sections of this specification.

The words "a", "an" and "the" are employed to describe elements and components of the invention. This is done merely for convenience and to give a general sense of the invention. This description should be read to include one or at least one and the singular also includes the plural, unless the context clearly indicates otherwise. Thus, for example, the term "an excipient" includes a reference to a single excipient, as well as a plurality of excipients, (including mixtures of excipients) and reference to "the excipient" generally includes reference to one or more excipients. It should also be noted that the term "or" is generally employed in its sense including "and/or" unless the content clearly dictates otherwise.

It will be understood that although the terms "first," "second," "third," "a)," "b)" and "c)," etc. may be used herein to describe various elements of the invention, the terms "first," "second," "third," "a)," "b)," and "c)," etc. are not intended to necessarily convey a sequence or other hierarchy to the associated elements but may be used for identification purposes only. The sequence of operations (or steps) is not limited to the order presented unless otherwise specifically indicated or implied to the contrary, such as by the context in which the referenced combination is made. Any combination of method or process steps as used herein may be performed in any order (and in some instances simultaneously), unless otherwise specifically indicated or implied to the contrary, such as by the context in which the referenced combination is made.

As used herein, the term "about" as used in relation to a numerical value is meant to encompass variations off ±50%, ±40%, ±30%, ±25%, ±20%, +15%, ±10%, ±5%, +3%, +2%, ±1%, ±0.5%, 0.25%, or even ±0.1% of the specified amount. Where necessary, the word "about" may be omitted from the definition or description of the invention.

The term "combining" as used herein in relation to the combination of two or more moieties is intended to be broadly interpreted. The term includes bringing the two or more moieties into association with each other in any suitable manner and in any desired or suitable order. In certain embodiments this may involve uniformly and intimately bringing the moieties together into association. In certain embodiments, the term "combining" may refer to admixing, blending, coating or to any other suitable means for combining the two or more moieties.

As used herein, the term "comprising" means "including". Thus, it is to be understood that the term "comprising" includes within its scope embodiments where one or more additional, unrecited elements are present, as well as the more restrictive term "consisting of" (i.e. where only the recited elements are present). The term "including" is to be likewise interpreted so as to encompass "including, but not limited to . . . ".

The term a "daily dose" as used herein can be in the form of a single tablet or capsule etc. or multiple tablets or capsules etc. to be taken on a given day. However, it is to be understood that the dosages may be varied depending upon the requirement of the patients and the severity of the condition being treated etc.

The term "herb" as used herein includes a reference to a plant valued for its medicinal properties and to any part of the plant or matter derived from the plant (e.g. herbal extracts or decocts) which contain active constituent(s) of the herb, and preferably the principal medically active constituent(s) of the herb. One example of a herb is a TCM of plant origin, but other herbs are envisaged such as materials of plant origin used in Kampo or Ayruvedic medicine etc.

The term "neuroconditioning" as used herein includes a reference to pharmacologically induced molecular events preventing or reducing possible future brain damage. Neuroconditioning results in providing tolerance to the brain against an ischaemic, epileptic or other injurious event. The effect is similar to preconditioning (a clinical and experimental approach demonstrated to be effective), but does not require exposure to stressful stimuli. Neuroconditioning induces prophylactically a tolerance in a patient, such as those at risk of an insult. Examples of such insults include insults resulting from a condition selected from the group consisting of: ischemic, transient or permanent, focal or generalized; seizure, focal or generalized; inflammatory; toxic (e.g. radiation, chemical, or drug-related); immunologic; infectious; metabolic, nutritional; traumatic; compressive; neoplastic; degenerative; genetic, congenital; and procedural (including for example those requiring general anesthesia, clamping of major vessels, or opening of the cranial cavity).

The term "neuroprotection" as used herein includes a reference to the preservation of neuronal tissue at risk of dying, such as during stroke or in the aftermath of a stroke. The term "neuroprotection" (and for the avoidance of doubt, grammatical variants thereof) may accordingly refer to the stimulation or promotion of cell survival, or prevention of cell death, where the cell is at risk of cell death, such as where the cell has been traumatised and would under normal circumstances (i.e. without intervention/treatment), with a high probability die.

Neuroprotection can be used to protect cells from stress (e.g. lack of oxygen, lack of glucose, glutamate stress, free radicals) within the nervous system, such as within the brain. Also by promoting survival it is possible to prevent or slow down diseases or prevent or slow down further degeneration of the nervous system in individuals suffering from a degenerative disorder.

The term "stroke" refers to the sudden death of tissue cells due to a lack of oxygen when the blood flow is impaired by blockage or rupture of an artery. Stroke is a vascular accident that can occur in the brain or in the cardiac system. The latter condition is medically known as "myocardial infarction" and more commonly known as a "heart attack". A cerebral stroke includes ischemic and haemorrhagic cerebral stroke.

The term "treatment" as used herein is intended to be construed broadly and includes a reference to any and all uses which remedy a disease or disorder, or symptoms of a disease or disorder (e.g. reduce the severity of the disease/disorder or symptoms thereof, reduce the frequency of symptoms etc.), prevent the establishment of disease/disorder, or otherwise prevent, hinder, retard, or reverse the progression of disease/disorder or other undesirable symptoms in any way whatsoever, even if the treatment is ultimately unsuccessful. Treatment may be in respect of a patient which already has the disease/disorder, or in respect of a patient which is prone to have the disease/disorder or in whom the disease/disorder is to be prevented. Thus, the term "treatment" (and for the avoidance of doubt, grammatical variants thereof such as "treating" etc.) may refer to therapeutic treatment or to prophylactic or preventative treatment.

The term "unit dosage form" (and similar expressions such as 'unit dose') refers to a single drug delivery entity, e.g. a tablet, capsule or sachet, with preferred unit dosage forms being those containing a daily dose or unit, daily sub-dose, or an appropriate predetermined amount of the extract.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Unless otherwise indicated, all technical and scientific terms used herein have the same meaning as commonly understood to one of ordinary skill in the art to which the invention belongs.

DETAILED DESCRIPTION OF THE PREFERRED EMBODIMENTS

Figure 1:
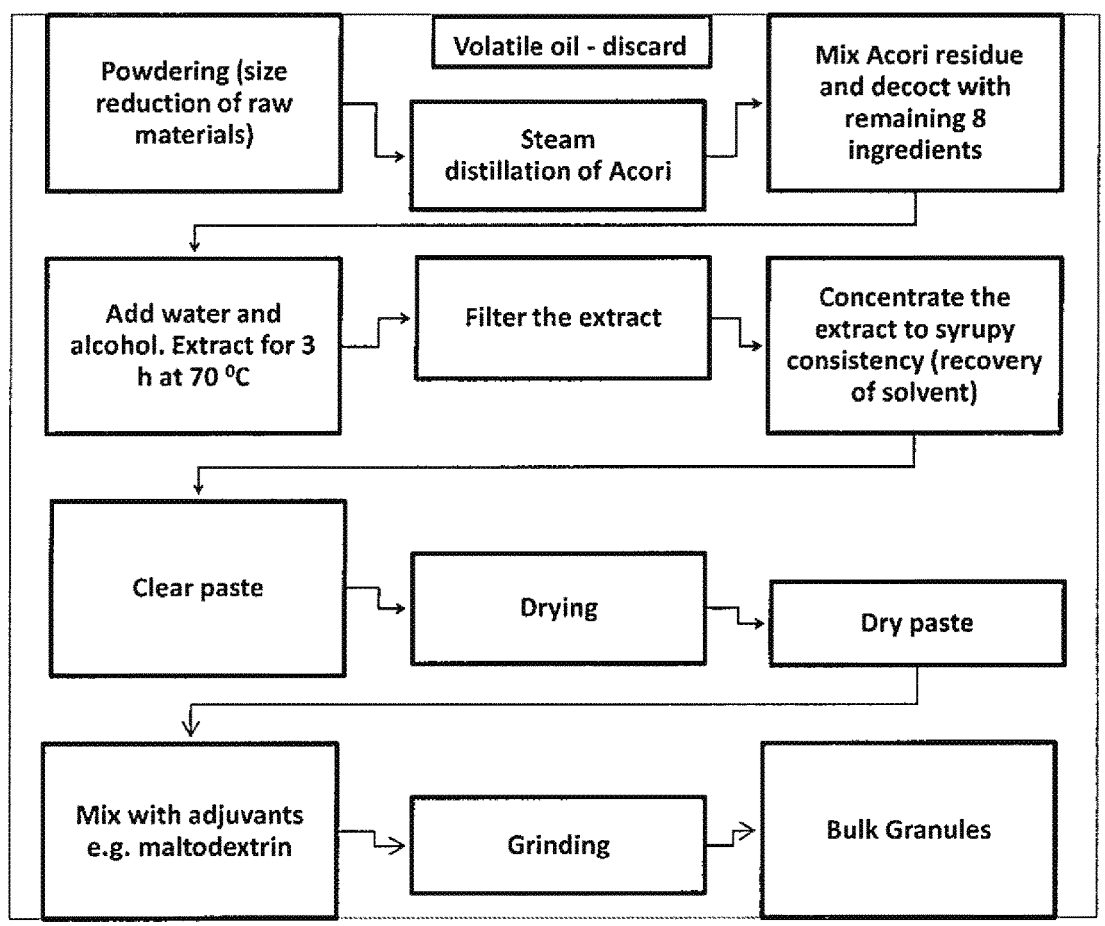
FIG. 1: Schematic of one embodiment of the process for producing bulk granules from nine herbs.
Figure 2:
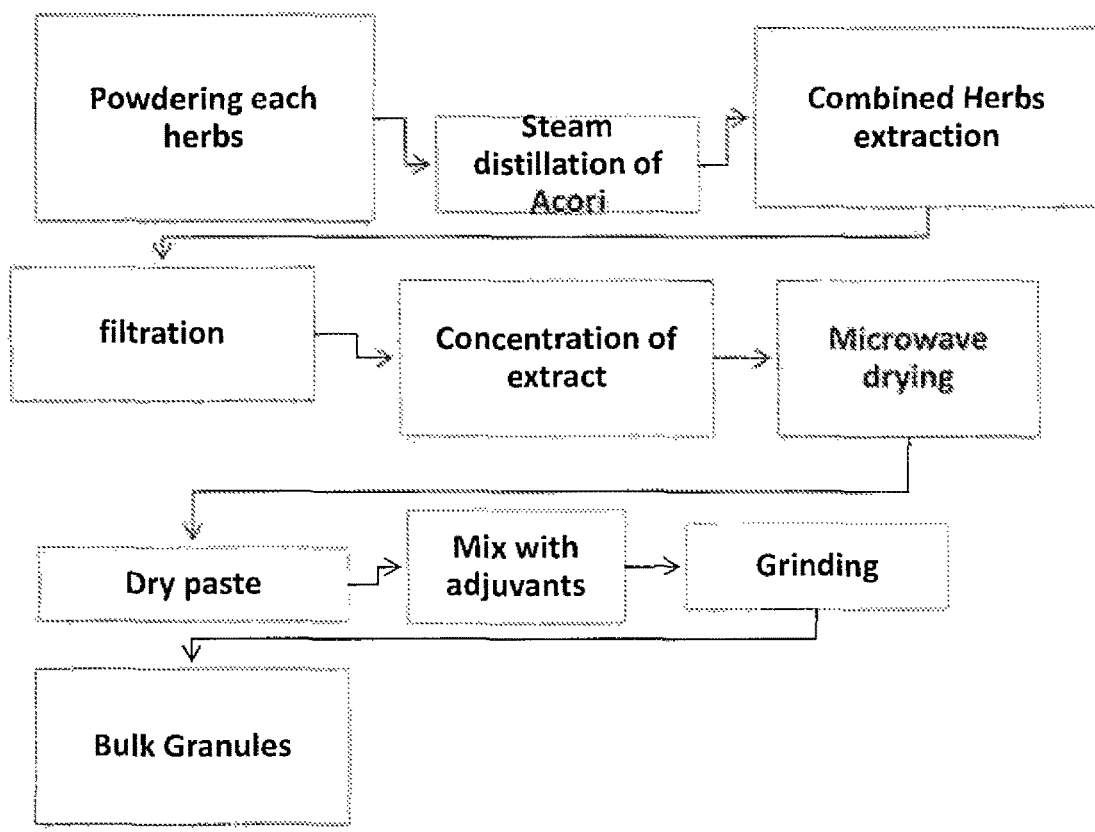
FIG. 2: Schematic showing an overview of one embodiment of the process for producing bulk granules from nine herbs.
Figure 3:
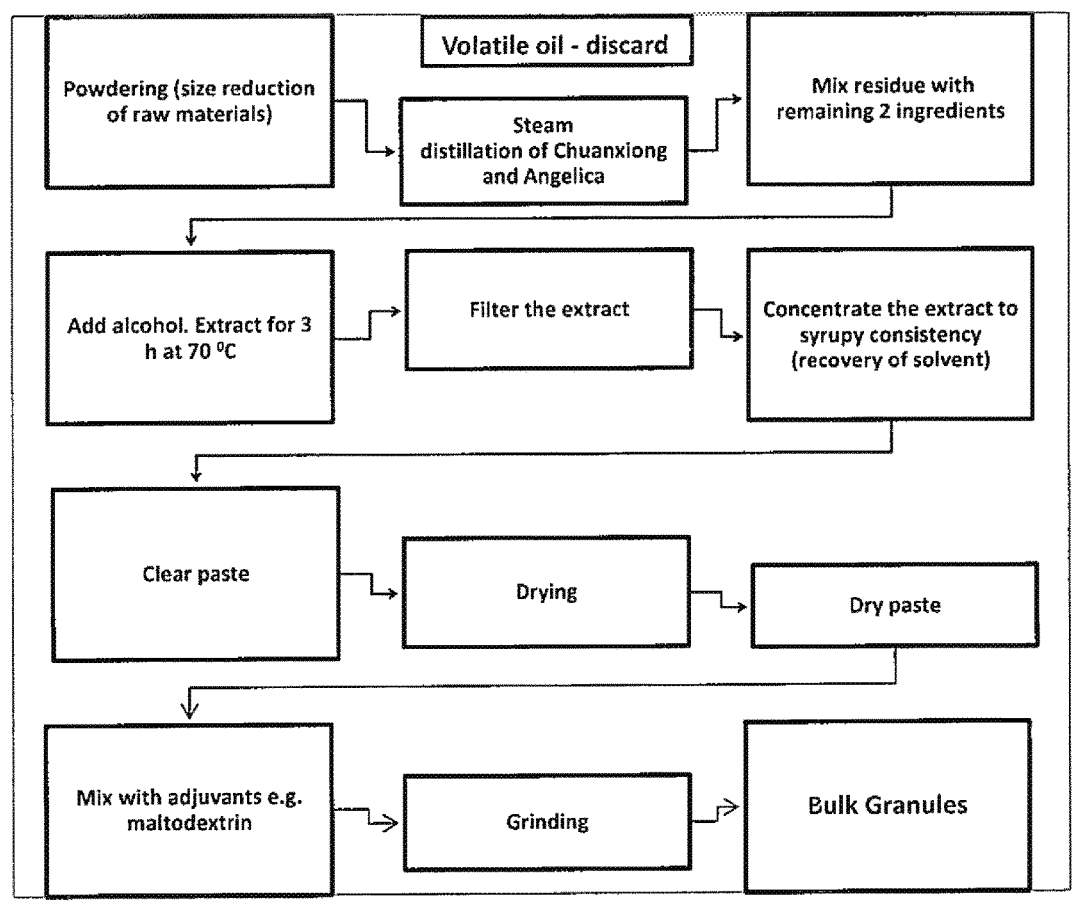
FIG. 3: Schematic of one embodiment of the process for producing bulk granules from four herbs.

The present invention provides a new and improved process for producing MLC901 as well as herbal products comprising the nine TCM herbal extracts of MLC901, together with sub-combinations thereof, wherein the sub-combinations include extracts derived from the following four herbs:
(i) *Radix Astragali* (root of Membranous Milkvetch or Huang Qi);
(ii) Rhizome of *Ligusticum Chuanxiong* (Chuan Xiong);
(iii) *Radix Angelicae sinensis* (root of Chinese *Angelica* or DanGui); and
(iv) *Radix Polygalae* (root of thinleaf milkwort, *Polygala tenuifolia* Willd., *Polygala sibirica* L. or Yuanzhi).

As shown in Table 1, MLC901 (also known as NeuroAiD II) is composed of nine natural plant ingredients or herbs. These herbs are all TCM herbs.

TABLE 1

| TCM used in MLC901 | |
| --- | --- |
| TCM/Herb | Part used |
| *Radix Astragali* (root of Membranous Milkvetch or Huang Qi) | Roots |
| *Radix* et *Rhizoma Salviae Miltiorrhizae* (Red Sage root or Dan Shen), | Roots & rhizomes |
| *Radix Paeoniae rubra* (Red Peony root) | Roots |
| Rhizome of *Ligusticum Chuanxiong* (Chuan Xiong) | Stem/rhizome |
| *Radix Angelicae sinensis* (root of Chinese Angelica or DanGui) | Roots |
| Flower of *Carthamus Tinctorius* (Safflower or HongHua) | Flower |
| *Semen Persicae* (*Prunus Persica* seeds or Taoren) | Ripe seeds |
| *Radix Polygalae* (root of thinleaf milkwort, *Polygala tenuifolia* Willd., *Polygala sibirica* L. or Yuanzhi) | Roots |
| *Rhizoma Acori tatarinowii* (rhizome of grassleaf sweetflag or Shichangpu) | Stem/rhizome |

A first aspect of the invention provides a process for preparing a mixture of herbal extracts, wherein the process comprises heating the herbs:
(I) *Radix Astragali* (root of Membranous Milkvetch or Huang Qi);
(ii) Rhizome of *Ligusticum Chuanxiong* (Chuan Xiang);
(iii) *Radix Angelicae sinensis* (root of Chinese *Angelica* or DanGui); and
(iv) *Radix Polygalae* (root of thinleaf milkwort, *Polygala tenuifolia* Willd., *Polygala sibirica* L. or Yuanzhi) in an aqueous organic solvent, to produce a solution containing the herbal extract mixture.

In one embodiment, the process may also optionally include the extraction of one or more additional herbs selected from:
a) *Radix* et *Rhizoma Salviae Miltiorrhizae* (Red Sage root or Dan Shen);
b) *Radix* Paeoniae *rubra* (Red Peony root):
c) Flower of *Carthamus Tinctorius* (Safflower or HongHua);
d) *Semen Persicae* (*Prunus Persica* seeds or Taoren); and
e) *Rhizoma Acori tatarinowii* (rhizome of grassleaf sweetflag or Shichangpu).

Optional sequential steps subsequent to the extraction process described above are:
i. separating particulate matter from the extraction solution;
ii. concentrating the extraction mixture by removing the solvent; and
iii. drying the concentrated extraction mixture to yield a dried extraction product.

In one embodiment, nine herbs are used in the extraction process, namely (i), (ii), (iii) and (iv) above, together with a), b), c), d) and e) above.

In another embodiment, only four herbs are used in the extraction process, namely (i), (ii), (iii) and (iv) above.

In other embodiments at least the four herbs (i), (ii), (iii) and (iv) above are used in the extraction process, together with 1, 2, 3 or 4 of the herbs a), b), c), d) and e) above.

In another embodiment, the product derived from the nine herbs, (i), (ii), (iii) and (iv) together with a), b), c), d) and e) above, is mixed with one or more TCMs of animal origin, including one or more of: *Buthus martensii, Eupolyphaga Seu Setelephaga, Calculus Bovis Artifactus, Cornu Saigae Tataricae* and *Hirudo*.

In certain embodiments, the herbal extracts or herbal products prepared by the process of this invention may further comprise one or more additional active ingredients, including one or more TCM extracts derived from plants (e.g. herbs) and/or of animal origin, one or more natural active ingredients, one or more pharmaceutical compounds, or mixtures thereof. When present, additional herbal extracts may be produced or sourced separately and combined with the extracts prepared by the process of this invention. If appropriate, additional herbal extracts may also be prepared using the process of this invention, conveniently in a "one-pot" method where all the herbs are extracted together.

In a further embodiment, one or more of the herbs may be subjected to one or more pre-treatment steps before being extracted according to the process of this invention. The pre-treatment step(s) may produce herbs in a more convenient or more suitable form for use as starting material in the process of the present invention. Examples of pre-treatment steps include: cleaning, drying, and increasing the surface of area of the herbs (e.g. by crushing or size reduction), and combinations thereof. In one embodiment, one or more herbs are cleaned, (e.g. by washing with water) to remove dirt or soil particles and the like.

Whilst the process of the invention can be performed on freshly harvested herbal material, it may be desirable to use dried herbs. Thus, in one particular embodiment of the invention, one or more (e.g. all) of the herbs are dried before being extracted. Suitable methods for drying herbs will be known in the art, and include air drying and heating.

The herbs selected for the extraction process of this invention may also be pre-treated to increase their surface area. For example, the herbs may be reduced in size to yield particles (e.g. a powder), smaller pieces of the herbs, or a mixture thereof. The size of the herbal material may influence the yield of the resulting extract. The selected herbs may be pre-treated together or individually to increase their surface area and, if the latter, the individual herbs subsequently combined before extraction.

Suitable size-reduction methods will be known to those skilled in the art, e.g. crushing, chopping or powdering. The herbs can also be frozen (e.g. in liquid nitrogen) and then crushed or fragmented into smaller pieces or particles such as powder.

Powdering or pulverising (the terms may be used interchangeably) may be achieved by any suitable means, such by using a grinding or milling machine. Where a grinding machine or the like is used, slow rpm with a big mesh size can be used to produce herbal material of a relatively larger size (such as chopped pieces), whereas a high speed and small mesh size (e.g. #8-10) will result in a powder. Particles larger than the mesh will remain in the machine and may be subjected to further be grinding. Non-limiting examples of grinding machines that may be used include a hammer mill, ball mill, and cylinder mill.

Where filtration is used in the process, the herbs should be appropriately sized to mitigate the blocking of the pores of the filter. If the herbal material is too coarse it may make extraction slower and less efficient.

The particle size of powdered herbal material may be up to about 3.5 mm, up to about 3 mm, up to about 2.7 mm, up to about 2.5 mm, up to about 2.4 mm, up to about 2.3 mm, up to about 2.2 mm, up to about 2.1 mm, up to about 2 mm or up to about 2.0 mm, up to about 1.9 mm, up to about 1.8 mm, up to about 1.7 mm, up to about 1.6 mm, or up to about 1.5 mm. In one embodiment, the particle size is up to about 2.6 mm, 2.5 mm, up to about 2.4 mm, up to about 2.3 mm, up to about 2.2 mm, up to about 2.1 mm, up to about 2 mm or up to about 2.0 mm, up to about 1.9 mm, or up to about 1.8 mm. In another embodiment, the particle size is up to about 2.4 mm, or up to about 2 mm.

In certain embodiments, powdered herbal material is passed through a mesh, such as a size 8 or 10 mesh, to produce herbal material of a desired size. The mesh size number is based on the U.S. mesh size standard, where size 8 corresponds to a 2.38 mm opening and size 10 corresponds to a 2.00 mm opening. Thus, particles having a size up to about 2.00 mm may be obtained using a size 10 mesh, and particles having a size up to about 2.38 mm may be obtained using a mesh of size 8.

In certain embodiments, one or more of the herbs are pre-treated before extraction by is fragmenting the herbs into small pieces, e.g. pieces of about 5 cm or less, about 4 cm or less, about 3 cm or less, about 2.5 cm or less, about 2 cm or less, about 1.5 cm or less, about 1 cm or less, or about 0.5 cm or less.

In certain embodiments, one or more of the herbs is powdered and one or more of the herbs is in small pieces prior to extraction. Embodiments are also envisaged wherein one or more of the herbs is a mixture of powdered herb and small pieces of herb. Accordingly, each of the herbs may be powdered, in small pieces, or a mixture of powdered herb and small pieces of herb.

In a particular embodiment, the herbs are pre-treated by:
(i) cleaning;
(ii) drying; and/or
(iii) increasing the surface area, e.g. by forming particles (e.g. a powder) and/or smaller pieces of herb.

The one or more pre-treatment steps may be performed in any suitable order. Notwithstanding this, it may be desirable to perform (i), (ii) and (iii) above in order.

The desired amount of each herb used in the process of the present invention may be measured out at any suitable pre-treatment stage, for example, after drying or increasing the surface area of the herb.

In one embodiment, *Radix* et *Rhizoma Salviae Miltiorrhizae* and *Radix Astragali* are used in the process of the present invention. The dry weight ratio of *Radix* et *Rhizoma Salviae Miltiorrhizae* to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, *Radix Paeoniae rubra* (Red Peony root) and *Radix Astragali* are used in the process of the present invention. The dry weight ratio of *Radix Paeoniae rubra* (Red Peony root) to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, Rhizome of *Ligusticum Chuanxiong* (Chuan Xiong) and *Radix Astragali* are used in the process of the present invention. The dry weight ratio of Rhizome of *Ligusticum Chuanxiong* (Chuan Xiong) to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, *Radix Angelicae sinensis* and *Radix Astragali* are used in the process of the present invention. The dry weight ratio of *Radix Angelicae sinensis* to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, the flower of *Carthamus Tinctorius* (Safflower or HongHua) and *Radix Astragali* are used in the process of the present invention. The dry weight ratio of the flower of *Carthamus Tinctorius* to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, *Semen Persicae* (*Prunus Persica* seeds or Taoren) and *Radix Astragali* are used in the process of the present invention. The dry weight ratio of *Semen Persicae* to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, *Radix Polygalae* (root of thinleaf milkwort, *Polygala tenuifolia* Willd., *Polygala sibirica* L. or Yuanzhi) and *Radix Astragali* are used in the process of the present invention. The dry weight ratio of *Radix Polygalae* to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

In another embodiment, *Rhizoma Acori tatarinowii* (rhizome of grassleaf sweetflag or Shichangpu) and *Radix Astragali* are used in the process of the present invention. The dry weight ratio of *Rhizoma Acori tatarinowii* to *Radix Astragali* may be, for example, in the range of about 1:2 to about 1:10; or in the range of about 1:2.5 to about 1:9; or in the range of about 1:3 to about 1:8; or in the range of about 1:3.5 to about 1:7; or in the range of about 1:4 to about 1.6; or in the range of about 1 to about 5.

It will be understood that freshly harvested or 'wet' herbs may also be employed in the present invention. Where fresh or 'wet' herbs are employed, the dry weight ratios referred to hereinbefore and hereinafter are the dried weight equivalent of the wet weight of the fresh herbs.

When *Rhizoma Acori tatarinowii* (rhizome of grassleaf sweetflag or Shichangpu) is used in the process of the present invention, it may be desirable to reduce the levels of any potentially toxic essential (also referred to herein as "volatile") oils, generally before (but potentially after) carrying out the extraction process. For convenience, this herb may also be referred to herein as '*Acori*' or '*Acori rhizoma*'. In particular, it may be desirable to reduce the level of asarone (e.g. the alpha and beta isomers thereof) which are major constituents in the essential oil of Acori, so as to enable, or facilitate, the production of the herbal product with a non-toxic level of asarone whilst retaining some of the asarone due to its beneficial therapeutic properties. Safe limits for beta asarone consumption have been set at 0.115 mg per person per day (equivalent to 0.002 mg/kg body weight/day) (see Chen et al. Planta Med 2009 Oct. 8:75(13): 1448-52. Epub 2009 Jun. 8). Obviously, the amount of beta asarone that can safely administered to a patient will not only depend on the amount or concentration of beta asarone within the product, but also the dose of the product received by the patient. Beta asarone content can be analysed using any suitable method, such as gas chromatography or HPLC.

In certain embodiments, the level of alpha and beta asarone present may be reduced by distillation, such as by steam distillation or hydro-distillation. Parameters during the process which can be used to control the concentration of asarone in the Acori distillate include the time of distillation and the volume of distillates and oil phase in distillates.

Where steam distillation is used, a sufficient amount of water will generally be used to wet the bed of Acori. During steam distillation, steam is injected to the distillatory from another tank (e.g. boiler).

When determining a suitable volume of water to use for hydro-distillation or steam distillation, considerations will typically include the amount of Acori present, the capacity of the distillation vessel, the time for distillation, and cost. Excessive use of water will slow down the process as it will take longer to boil/evaporate and will also require more energy. Conversely if too little water is used then not enough oil will be separated. The desired alcohol concentration in the extraction step may also be taken into account since the alcohol concentration of the extraction mixture will be dependent on the amounts of water and alcohol added to the extractor and excessive use of water in the distillation of Acori will result in a more dilute decoct which, when added to the extractor, may result in an extraction mixture having an alcohol concentration lower than the desired alcohol concentration.

The hydro-distillation or steam distillation may conveniently be performed at atmospheric pressure, although it may also be performed at an elevated pressure.

In one embodiment, distillation is continued until the oil is substantially completely distilled off.

In certain embodiments, the dry weight (g) ratio of the Acori used in the distillation step to the volume of the Acori decoct resulting from distillation (ml) ranges from about 1:3 (g/ml) to about 1:35 (g/ml), or from about 1:5 (g/ml) to about 1:30 (g/ml), or from about 1:7 (g/ml) to about 1:30 (g/ml), or from about 1:7 (g/ml) to about 1:27 (g/ml), or from about 1:7 (g/ml) to about 1:25 (g/ml), or from about 1:8 (g/ml) to about 1:23 (g/ml).

In certain embodiments, the dry weight (g) ratio of the Acori used in the distillation step to the volume of the Acori decoct resulting from distillation (ml) ranges from about 1:5 (g/ml) to about 1:15 (g/ml), or from about 1:7 (g/ml) to about 1:13 (g/ml), or from about 1:8 (g/ml) to about 1:12 (g/ml), or from about 1:9 (g/ml) to about 1:11 (g/ml), or from about 1:10 (g/ml).

In certain embodiments, the dry weight (g) ratio of the Acori used in the distillation step to the volume of the Acori decoct resulting from distillation (ml) ranges from about 1:10 (g/ml) to about 1:30 (g/ml), or from about 1:15 (g/ml) to about 1:25 (g/ml), or from about 1:17 (g/ml) to about 1:23 (g/ml), or from about 1:19 (g/ml) to about 1:21 (g/ml), or about 1:20 (g/ml).

The Acori along with the decoct may be used in the subsequent extraction process of this invention along with the other herbs.

Suitably, the Acori and the other herbs are used in accordance with the ratios mentioned above. The weight of Acori used, when referencing the aforementioned ratios, is taken to be the weight of Acori to produce the Acori and decoct which is added to the extractor.

In certain embodiments, at least part of the distillate is used in producing the herbal extract or herbal product of this invention. When at least part of the aqueous phase of the distillate is used, it is either introduced into the container comprising the Acori residue and decoct, or added to the extractor along with the Acori residue and decoct and other herbs to be extracted. When at least part of the oil phase of the distillate is used, the oil may be introduced at any suitable step in the process. Where the oil is added to one or more of the other herbs (which may, for example, be in the form of a liquid extract, bulk product e.g. bulk granules, etc.), the herbal material to which the oil is added is substantially dry so as to facilitate absorption of the oil. Suitably, the oil is added to the one or more other herbs at a stage of the process when the one or more other herbs is/are no longer exposed to heat. Typically, the oil will be added towards the end of the process of the invention, and in one embodiment is added to a bulk product of the invention (e.g. bulk granules), optionally also with a lubricant (e.g. magnesium stearate).

In certain embodiments, the oil may be sprayed onto product (e.g. bulk product) prior to packing, for example, in accordance with the method(s) described in CN1965966.

In certain embodiments, about 5%, about 10%, about 20%, about 30%, about 40%, about 50%, about 60%, about 70%, about 80%, about 90% or about 95% of the oil is used. Optionally less than about 5%, less than about 10%, less than about 20%, less than about 30%, less than about 40%, less than about 50%, less than about 60%, less than about 70%, less than about 80%, less than about 90% or less than about 95% of the oil is used. Optionally up to about 5%, up to about 10%, up to about 20%, up to about 30%, up to about 40%, up to about 50%, up to about 60%, up to about 70%, up to about 80%, up to about 90% or up to about 95% is used. Optionally, about 5% to about 95%, about 10% to about 90%, about 20% to about 80%, about 30% to about 70%, about 40% to about 60%, about 10% to about 50%, about 10% to about 40%, about 5% to about 35%, about 5% to about 30%, about 5% to about 25%, about 5% to about 20%, about 5% to about 15%, or about 5% to about 10% of the oil is used.

Other methods for reducing the level of asarone in the herbal extract/product include: (1) removing the volatile oil by supercritical fluid extraction using carbon dioxide fluid [see Puri R. K. (1998) Indian J. Nat. Prod., 14(2), 3)] and (2) decoction (boiling water extraction). Methods for preparing herbal decoctions are described in the TCM Working Party of the European Pharmacopeia for producing decoctions. See also Chen et al. Planta Med 2009 Oct. 8; 75(13):1448-52. Epub 2009 Jun. 8 which describes an extended decoction for beta asarone reduction.

In one embodiment, the process of the present invention includes removing volatile oil from *Radix Angelicae sinensis* and/or *Chuanxiong*, e.g. prior to extraction of the herbs. The volatile oil may, if appropriate, be added to the product at a later stage of the process, such as to bulk product of the invention. This may provide a beneficial effect in terms of the biological activity of the resulting product. The methods described above for removing the volatile oil in Acori are also applicable to *Radix Angelicae sinensis* and *Chuanxiong*. Similarly, the herbal decoct and herbal residue resulting from distillation may conveniently be used in the extraction step of the invention, with the volatile oil reserved for potential later use.

The aqueous organic solvent used in the extraction process (a) of this invention may be, for example, a hydro-alcoholic solvent. The alcohol component of the hydro-alcoholic solvent may be selected from alcohols which have sufficient miscibility with water to form a hydro-alcoholic solvent. Selection of the alcohol may also take into consideration the intended use of the herbal extract or herbal product such as the suitability (e.g. the toxicity) of the alcohol for extraction of products to be used in medicaments or other compositions for human or animal consumption. Non-limiting examples of alcohols suitable for use as part of the hydro-alcoholic solvent include C2, C3 or C4 alkanols, including ethanol, isopropanol, and propanol or a mixture thereof. Preferably, the alcohol in the hydro-alcoholic solvent comprises or consists of ethanol. In another embodiment, we provide an aqueous alcoholic solvent comprising a mixture of ethanol and isopropanol. A particular embodiment is ethanol:isopropanol:water in a ratio of 40:30:30.

The aqueous organic solvent used in the extraction process (a) of this invention may also be, for example, aqueous acetone or propylene glycol, optionally also comprising a C2, C3 or C4 alkanol, e.g. ethanol.

In certain embodiments of the invention, the concentration of alcohol (e.g. ethanol) in the hydro-alcoholic solvent may be in the range of about 30% (v/v) to about 90% (v/v), about 35% (v/v) to about 90% (v/v), about 35% (v/v) to about 85% (v/v), or about 35% (v/v) to about 80% (v/v). In other embodiments, the concentration of alcohol (e.g. ethanol) in the hydro-alcoholic solvent may be in the range of about 50% (v/v) to about 80% (v/v), about 55% (v/v) to about 75% (v/v), about 60% (v/v) to about 70% (v/v), about 63% (v/v) to about 70% (v/v), or about 65% to about 69% (v/v), about 70% (v/v) to about 90% (v/v), about 75% (v/v) to about 85% (v/v), about 77% (v/v) to about 83% (v/v), about 30% (v/v) to about 50% (v/v), about 35% (v/v) to about 45% (v/v), or about 38% (v/v) to about 42% (v/v).

In a particular embodiment, the concentration of alcohol (e.g. ethanol) in the hydro-alcoholic solvent may be in the range of about 50% (v/v) to about 90% (v/v), more particularly about 57% (v/v) to about 88% (v/v); more particularly about 60% (v/v) to about 85% (v/v); more particularly about 63% (v/v) to about 82% (v/v); more particularly about 65% (v/v) to about 80% (v/v); more particularly about 68% (v/v) to about 78% (v/v); more particularly about 69% (v/v) to about 75% (v/v); more particularly about 70% (v/v) to about 74% (v/v); more particularly about 71% (v/v) and about 73% (v/v); and more particularly about 72% (v/v).

The concentration of alcohol in the extraction mixture will depend on, amongst other factors, the volume and concentration of alcohol used to form the extraction mixture. Other factors will include the volume of water or other liquids added to the extractor. Such other liquids may, for example, include an aqueous decoct of Acori, Rhizome of *Ligusticum Chuanxiong*, and/or *Radix Angelicae sinensis* as obtained from distillation of the same to remove or reduce the volatile oil in the herb(s).

In certain embodiments, the extraction mixture is formed by adding the herbs and organic solvent, such as an alcohol (e.g. ethanol) to the extractor. Typically water will also be added to the extractor, although if a large amount of aqueous herbal decoct is added to the extractor then it may not be necessary to add water. The desired organic solvent (e.g. alcohol) concentration may be obtained by adjusting the amount of water (if used) and organic solvent (e.g. alcohol) added to the extraction mixture. The herbs, water (if used) and organic solvent (e.g. alcohol) may be combined prior to addition to the extractor, and/or combined within the extractor.

The herbs are preferably added to the extractor in a predetermined ratio. Suitable ratios are discussed above. A preferred ratio for the herbs of the invention is a dried weight ratio of about 1:1, with the exception of *Radix Astragali* which may, for example, be in a dried weight ratio of about 5:1 (w/w) ratio to each of the other used herbs.

In certain embodiments, the alcohol used in the extraction process of the invention is ethanol having an initial concentration (i.e. the concentration prior to being diluted with water before and/or as part of the extraction process) of greater than about 90% (v/v), 91% (v/v), 92% (v/v), 93% (v/v), 94% (v/v), 95% (v/v), 96% (v/v), 97% (v/v), 97.5% (v/v), 98% (v/v), 98.5% (v/v), 99% (v/v), 99.1% (v/v), 99.2% (v/v), 99.3% (v/v), 99.4% (v/v), 99.5% (v/v), 99.6% (v/v), 99.7% (v/v), 99.8% (v/v), or 99.9% (v/v).

In certain embodiments the selected herbs which are added to the extractor are dried (e.g. dried powdered herb, dried herb fragmented into smaller pieces, or mixtures thereof). Alternatively, where the selected herbs comprise *Rhizoma Acori tatarinowii*, Rhizome of *Ligusticum Chuanxiong* or *Radix Angelicae sinensis*, these may be added to the extractor as a residue and decoct of the herb, e.g. such as that produced following removal or reduction of volatile oil as described herein.

*Rhizoma Acori tatarinowii* may be added to the extractor in the form of an Acori residue and decoct, e.g. such as that produced following removal or reduction of asarone as described herein, or as a dried herb (e.g. dried powder or dried herb fragmented into smaller pieces).

Rhizome of *Ligusticum Chuanxiong* may be added to the extractor in the form of a Rhizome of *Ligusticum Chuanxiong* residue and decoct, e.g. such as that produced following removal of volatile oil as described herein, or as a dried herb (e.g. dried powder or dried herb fragmented into smaller pieces).

*Radix Angelicae sinensis* may be added to the extractor in the form of a *Radix Angelicae sinensis* residue and decoct, e.g. such as that produced following removal of volatile oil as described herein, or as a dried herb (e.g. dried powder or dried herb fragmented into smaller pieces).

Each of the other herbs used may conveniently be added to the extractor as a dried herb (e.g. dried powder or dried herb fragmented into smaller pieces).

Suitable extractor vessels for use in the extraction step (a) of the present invention will be known to those skilled in the art. As an example, the extractor vessel may be an extractor tank with a stirrer (e.g. a long blade turning around in the bottom or middle of the extractor at low speed); the tank may optionally also possess a chopper. Alternatively, a tank which possesses neither stirrer nor chopper may be used, and operates by using the movement/the stream created by heat (e.g. boiling). In certain embodiments, the extractor may be a jacketed extractor fitted with stirrer and condenser. In line with good manufacturing practice, the extractor is suitably made of stainless steel. Preferably, during extraction the herbal material is homogenized.

In one embodiment, the extraction process of the invention is conducted at a temperature below 100° C. (e.g. from about 50° C. to about 90° C.). This temperature enables increased efficiency and improved safety, and is also beneficial in minimising loss of bioactives within the herbs which may be unstable at higher temperatures. A convenient temperature may be less than about 80° C., less than about 78° C., less than about 75° C., less than about 73° C., less than about 72° C., less than about 71° C., less than about 70° C., less than about 69° C., less than about 68° C., less than about 67° C., less than about 66° C., or less than about 65° C. In particular, the extraction process of the invention is conducted at a temperature in the range of about 55° C. to about 80° C.; in the range of about 57° C. to about 80° C.; in the range of about 60° C. to about 70° C.; in the range of about 60° C. to about 75° C.; in the range of about 62° C. to about 75° C.; in the range of about 62° C. to about 73° C.; in the range of about 62° C. to about 72° C.; in the range of about 62° C. to about 71° C.; in the range of about 62° C. to about 70° C.; in the range of about 62° C. to about 69° C.; in the range of about 63° C. to about 75° C.; in the range of about 63° C. to about 73° C.; in the range of about 65° C. to about 73° C.; in the range of about 63° C. to about 72° C., in the range of about 64° C. to about 71° C., or in the range of about 65° C. to about 71° C. In certain embodiments, the extraction mixture is heated and maintained at a temperature in the range of about 60° C. to about 75° C.; in the range of about 61° C. to about 74° C.; in the range of about 62° C. to about 73° C.; in the range of about 63° C. to about 72° C.; in the range of about 64° C. to about 71° C.; or in the range of about 65° C. to about 70° C.

In certain embodiments, the extraction mixture is heated and maintained at a temperature of about 60° C., about 62° C., about 63° C., about 64° C., about 65° C., about 66° C., about 67° C., about 68° C., about 69° C., about 70° C., about 71° C. or about 72° C.

The temperature of the extraction mixture is maintained for a suitable length of time for complete extraction to occur. In one embodiment, the extraction mixture is heated at a temperature of about 65° C. to about 70° C. for about 3 hours.

A suitable endpoint for extraction may be derived from the appearance and concentration of know biomarkers in the extract. Examples of suitable biomarkers are described in Table 2 below. Factors determining the appropriate endpoint include: yield of the chosen biomarkers peaks and concentration of the chosen biomarkers no longer increase, coupled with economic factors based on an assessment of the value of higher concentrations of the chosen biomarkers relative to the increased cost to continue the extraction process to obtain the higher concentrations.

In certain embodiments, the temperature of the extraction mixture may be maintained for about 30 minutes to about 360 minutes, for about 45 minutes to about 330 minutes, for about 45 minutes to about 300 minutes, for about 45 minutes to about 270 minutes, for about 60 minutes to about 240 minutes, for about 80 minutes to about 220 minutes, or for about 100 minutes to about 200 minutes. In one embodiment, the temperature of the extraction mixture is maintained for about 60 minutes to about 240 minutes. In certain embodiments, the temperature of the extraction mixture is maintained for about 30, 45, 60, 75, 90, 120, 150, 160, 170, 180, 190, 200, 210, 240, 270, 300, 330 or 360 minutes.

As will be appreciated from the discussion herein, the extraction process of the present invention is advantageous in that it does not require multiple extractions on the same mass. By avoiding multiple extractions, the process demonstrates an advantage over prior processes with respect to time to complete the extraction of herbal material, the energy used and consequently the cost of extraction. Also, the simplicity of the process (having fewer variables) increases the accuracy and reproducibility of the method, thus facilitating more consistent quality and/or activity across product batches.

The extraction process of this invention also potentially avoids, or at least minimizes, the production of unwanted material that may be extracted from the mass. Such material can be generated from multiple extractions of the same mass and includes, for example, carbohydrates, starches and proteins. Such unwanted material adds bulk to the product without contributing activity, thereby reducing the potency of the product.

Whilst the extraction process of the present invention does not require multiple extractions of the same mass, embodiments are envisaged where the process may comprise multiple extractions. For example, extraction of the herbs may be achieved by dividing the biomass of the herbs into two or more separate biomasses with each extraction extracting a different portion of the biomass.

In another embodiment, the extraction process of the present invention may modified by: (I) heating two or more extraction mixtures collectively comprising at least:
(i) *Radix Astragali* (root of Membranous Milkvetch or Huang Qi);
(ii) Rhizome of *Ligusticum Chuanxiong* (Chuan Xiong);
(iii) *Radix Angelicae sinensis* (root of Chinese *Angelica* or DanGui); and
(iv) *Radix Polygalae* (root of thinleaf milkwort, *Polygala tenuifolia* Willd., *Polygala sibirica* L. or Yuanzhi);
in an aqueous organic solvent, and (II) combining the extracted material to produce a single herbal extract of said herbs.

Where the extracted material is produced by two or more extractions this may, for example, entail extracting each of the herbs individually, extracting one or more of the herbs individually and extracting the remaining herbs in a combined extraction, or extracting sub-combinations of the herbs separately (e.g. extraction of some of the herbs by one run of the extraction step, whilst the remaining herbs are extracted by one or more further runs of the extraction step). Also envisaged is where portions of the same herb are extracted separately from each other, e.g. a herb may be di sided into two or more quantities with the two or more quantities being extracted separately from each other.

Where the extraction process of the invention is modified as above, the step of combining the extracted material to produce a single herbal extract may be performed at any suitable point in the process. In certain embodiments, the step of combing the extracted material to produce a single herbal extract is achieved by combining the extraction solutions after they have been separated from the particulate matter. Separation may, for example, be achieved by filtration with the individual filtrates then being combined to produce a single herbal extract. The combined extraction solutions may then be subject to further processing such as concentration and/or drying etc. Alternatively the individual filtrates may separately undergo solvent removal and/or drying prior to being combined.

After the extraction, the contents of the extraction tank are preferably cooled, e.g. to ambient temperature. Any suitable means for cooling the extraction mixture may be used. The contents of the extraction tank may, for example, be cooled by circulating cool water through the jacket of the extraction tank. Common practice is for the extract to be filtered to an empty tank or container which is then transferred to a cold room for cooling.

The extraction solution (which may also be referred to herein as 'the extract') may be further processed according to its intended utility which may, for example, be as a therapeutic and/or prophylactic herbal composition, a pharmaceutical composition, nutraceutical or phytoceutical. Considerations may optionally include the route of administration (which is preferably oral administration, although other routes of administration are envisaged) and the dosage form (e.g. whether a liquid or solid formulation, whether as tablets or capsules etc.).

Steps in the further processing of the extract may optionally include: separating the extraction solution from the particulate matter (e.g. by filtration), concentrating the extract, drying the extract, powdering the extract, granulating the extract to form granules (e.g. by dry granulation, wet granulation, or direct compression), forming bulk product of the extract (e.g. bulk granules), combining the extract with one or more further ingredients, preparing unit dosage forms comprising the extract, and mixtures of any two or more of the foregoing.

Where the extraction solution or extract of the invention is powdered (e.g. by using a fluid bed dryer), the powder can be made into bulk product such as bulk powder or bulk granules or used 'as is' to make a herbal product of the invention. Examples of the latter may include using the powder to make solid dosage forms such as tablets or capsules, or combining the powder with water or other liquid (e.g. sugar syrup) to make a liquid composition.

Typically, the further processing of the extract will comprise separating particulate matter in the extraction mixture from the extraction solution (e.g. by filtration) followed by concentration and/or drying. During processing, one or more further ingredients may be combined with the extract such as one or more excipients (e.g. a diluent and/or lubricant) and/or one or more further active ingredients [e.g. a pharmaceutical, or TCM ((Traditional Chinese Medicine)].

In a particular embodiment, a diluent (e.g. dextrin and/or maltodextrin and/or micro-crystalline cellulose in its free flowing forms) and/or a lubricant (e.g. a metal stearate, preferably magnesium stearate) may be combined with an extract of the invention, optionally with one or more further excipients (e.g. a glidant) and/or one or more further active ingredients (e.g. a pharmaceutical or further TCM ingredient). In certain embodiments, maltodextrin and a lubricant such as magnesium stearate may be combined with an extract of the invention. A lubricant may conveniently be used when the extract is in the form of granules.

In another embodiment, a diluent (e.g. dextrin and/or maltodextrin) and/or a glidant may be combined with an extract of the invention, optionally with one or more further excipients (e.g. a lubricant, such as a metal stearate, preferably magnesium stearate) and/or one or more further active ingredients (e.g. a pharmaceutical or further TCM ingredient). In certain embodiments, maltodextrin and a glidant may be combined with an extract of the invention. A glidant may conveniently be used when the extract is in the form of a powder. Optionally, where the extract is in the form of a powder the extract may be combined with a diluent (e.g. dextrin and/or maltodextrin), a glidant and a lubricant.

Non-limiting examples of glidants include silicon oxide derivatives, anhydrous colloidal silica (Aerosil 200), syloids, starch, magnesium stearate, glycerol monostearates, talc as well as others known in the art. Optionally, one or more glidants may be employed and accordingly two or more glidants may be combined with an extract of the invention, such as extract in the form of a powder.

In certain embodiments, the further processing of the extract may comprise preparing bulk product (e.g. bulk granules) comprising the extract and preparing a herbal product (e.g. pharmaceutical composition, capsules, tablets etc.) from the bulk product. Accordingly, the herbal products of the invention, such as dosage forms of the invention, may be made via bulk product. Such bulk product may provide a convenient or suitable means for storing and/or transporting the extract of the invention. In other embodiments, the step of bulk product formation may be omitted.

In certain embodiments, at least one pharmaceutically acceptable carrier, diluent or excipient may be combined with the extract (e.g., by admixing). In this way bulk product (e.g. bulk granules) or a dosage form comprising said extract and said one or more pharmaceutically acceptable carriers, diluents or excipients may be produced. Preferably the dosage form is an oral dosage form and/or a tablet or capsule.

Typically, the further processing of the extract may comprise separating particulate matter in the extraction mixture from the extraction solution (i.e. the liquid comprising the solvent and extracted herbal material). Separation may be by any suitable method, such as filtering or centrifugation. Separating includes at least partially separating the extraction solution from the particulate matter. In certain embodiments separating the extraction solution from the particulate matter results in removal of substantially all of the particulate matter from the extraction solution.

In a particular embodiment, the particulate matter in the extraction mixture may be separated from the extraction solution by filtration e.g. filtration using a mesh. The mesh may, for example, be of a size equal to, or less than, about 45, 40, 35, 30, 25 or 20 microns. In certain embodiments a mesh may be used of the size selected from the group consisting of: 15 to 50 microns; 15 to 45 microns; 18 to 40 microns; 18 to 35 microns; 20 to 45 microns; 20 to 40 microns; 18 to 30 microns; 18 to 25 microns; or 20 to 25 microns. A mesh size of about 18, 20, 22 or 25 microns may also conveniently be used; particularly a mesh size of about 20 microns.

Where the herbal material used in the extraction process comprises herbs which have been fragmented into smaller pieces (as opposed to for example powdered herb), filtration may employ a larger mesh size and selection of an appropriate mesh size or other means of filtration will be within the skill of those in the art.

In one embodiment, the extraction solution may be concentrated by solvent removal to yield concentrated extract, e.g. a paste or syrup. Prior to concentration of the extraction solution, particulate matter may conveniently be separated from the extraction solution as described above (e.g. by filtration). Accordingly, the extraction solution may, for example, be separated from particulate matter and the extraction solution then concentrated.

In particular embodiments, the extraction solution may be concentrated by solvent removal to yield a ratio of concentrated extract to extraction solution of about 250 g concentrated extract to about 5 litres of extraction solution. Suitably, this ratio may be varied by ±25%, ±20%, or ±15%; and more particularly by ±10%, or ±5%.

In certain embodiments, the solvent removal results in the extract being concentrated from the extraction solution by about 15 to about 25 fold; about 17 to about 23 fold; about 18 to about 22 fold; or about 19 fold, 20 fold or 21 fold. In other embodiments, a lower or higher degree of concentrating may be carried out, or the concentrating step omitted.

The techniques of solvent removal are known to those skilled in the art and include, but are not limited to, rotary evaporation, centrifugal vacuum evaporation or lyophilisation. An oven or a fluid bed dryer may also be used. A fluid bed dryer may remove the solvent and produce a powder product, in which case the drying step described below may be omitted.

To remove the solvent by evaporation, the temperature is suitably elevated to a little below the boiling temperature of the solvent. The boiling temperature of the solvent will also be dependent on the pressure. In certain embodiments, the extraction solution is concentrated under reduced pressure (e.g. 3-5 psi or 0.207-0.345 bar) and at an elevated temperature (i.e. at a temperature greater than ambient temperature). In particular embodiments, the temperature does not exceed about 80° C., about 78° C., about 75° C., about 73° C., about 72° C., about 71° C., about 70° C., about 69° C., about 68° C., about 67° C., about 66° C., or about 65° C.

In certain embodiments, the extraction solution is concentrated under reduced pressure and at a temperature in the range of about 55° C. to about 75° C.; about 55° C. to about 72° C.; about 55° C. to about 70° C.; about 57° C. to about 75° C.; about 57° C. to about 72° C.; about 57° C. to about 70° C.; about 60° C. to about 75° C.; about 60° C. to about 72° C.; about 60° C. to about 70° C.; or about 60° C. to about 65° C.

In certain embodiments, the extraction solution is concentrated under reduced pressure and at a temperature in the range of about 60° C. to about 70° C. The temperature may be, for example, about 60° C., about 62° C., about 65° C., or about 70° C.

Following concentrating and/or separating the extract from particulate matter as described above, the extract may conveniently be dried to yield a paste which still retains some moisture from the solvent. Where the extract has previously been concentrated by solvent removal, the drying process may convert the syrupy paste produced by the solvent recovery step into a dryish paste. In certain embodiments, the weight ratio of the product before and after the drying step is about 25 to about 18-19.

In other embodiments a greater degree of drying may be achieved. A greater degree of drying may be desirable where the later described granule formation step is omitted—this may for example be possible with the use of a fluid bed dryer. Conversely, the drying step may be omitted or a lower degree of drying carried out. This may, for example, be desirable where a liquid or semi-liquid formulation is desired.

If drying comprises the application of heat then this should be carefully performed, as the bioactive extracts may degrade when subjected to heat and, thus, activity can be deleteriously affected. In general, it may be preferable to heat for the shortest time possible to limit degradation. Any process known to one of skill that avoids any heating, or at least excessive heating may conveniently be used, including, for example, drying in a dessicator at room temperature, spray drying, vacuum drying, freeze-drying, critical point drying, solvent exchange, and any combination thereof known to one of skill. In certain embodiments, the extract may be dried by microwave drying, dry heat oven, tray drying or by RVD (Rotary Vacuum Drying).

The dried extract may be further processed according to intended use. In certain embodiments, the extract may be formulated into a bulk product (also referred to herein as stock product). The bulk product may then be used to prepare a herbal product of the invention such as a unit dosage.

In certain embodiments, the extract of the invention may be formulated as a 'final product' such as a therapeutic and/or prophylactic herbal composition, a pharmaceutical composition, nutraceutical or phytoceutical.

The extracts of the present invention may optionally be combined with one or more further ingredients. The one or more further ingredients may be combined with the extracts of the present invention at any suitable point during the process of the present invention as will be understood by those skilled in the art.

Non-limiting examples may include adding the one or more further ingredients to the extraction solution (before or after it is has been optionally separated from particulate matter), to the extract produced by the optional concentrating step, to the extract produced by the optional drying step, to the extract when in the optional bulk product form (e.g. bulk granules), during the production of the foregoing (e.g. during the process of granule formation or the forming of dosage form), during the formation of a dosage form comprising the extract (e.g. during the process of preparing the extract into the form of a capsule, tablet or the like), as a coating to a dosage form comprising the extract, or any combination of the foregoing. Different further ingredients may be added to the extract at different points of the process of the disclosure, and the same further ingredient may also be added to the extract at two or more points of the process of the disclosure.

Suitable methods for combining the one or more further ingredients with an extract of the present invention will be known to those skilled in the art. Such compositions may, for example, be prepared by admixing the extract with a further ingredient and/or by coating the extract (e.g. when the extract is in the form of granules or in a dosage form). Conventional pharmaceutical compounding techniques may suitably be used and reference may be made to the latest edition of Remington's Pharmaceutical Sciences (Maack Publishing, Easton Pa.).

Examples of the additional further ingredient(s) which may be combined with an extract of the invention (whether in the form of a solution of the extract, a syrupy or dryish paste of the extract, extract in the form of bulk product etc.) include, but are not limited to, the following: one or more further active ingredients (e.g. pharmaceutical compounds or compositions, other therapeutic agents; traditional medicine [e.g. TCM or Kampo medicine) etc.], fillers (also referred to herein as diluents); other herbs/herbal extracts/ herbal material; TCM ingredients which may optionally be of plant or animal origin; natural products derived from animals or animal products; preservatives; pharmaceutically acceptable additives, carriers, fillers (diluents), or excipients; and mixtures of two or more of the foregoing.

Non-limiting examples of further active or therapeutic agents include agents useful for treating one or more of the medical indications described herein for the herbal products of the invention, e.g. treating stroke, a neurodegenerative disorder (e.g. Alzheimer's or Parkinson's) or brain or nervous system trauma.

In certain embodiments, the one or more further active or therapeutic agent is selected from the group consisting of: antiplatelets (e.g. aspirin), anticoagulants, neuroprotectants, compounds for treating stroke and compounds for activating potassium channels TREK-1.

Non-limiting examples of excipients includes vehicles, binders, buffers, adjuvants, stabilizers, disintegrants, fillers (diluents), carriers, lubricants, suspending/dispersing agents, absorbents, granulating agents, glidants, colorants, additives, gums, coatings, antioxidants, preservatives, sweeteners, disintegration agents, suspending agents, granulating agents, desiccants, solvents, colorants, anti-adherents, antistatic agents, surfactants, plasticizers, emulsifying agents, flavoring agents, viscosity enhancers, antioxidants, and mixtures thereof. The excipient(s) may optionally be pharmaceutically acceptable.

In certain embodiments, an extract of the invention (e.g. when in the form of a solution of the extract, a syrupy or dryish paste of the extract, granules of the extract etc.) is combined with one or more pharmaceutically acceptable fillers (diluents). Non-limiting examples of fillers include starch, dextrin, maltodextrin, microcrystalline cellulose, talc, calcium carbonate, lactose, dextrose, sucrose, mannitol, anhydrous silicic acid, corn starch, crystalline cellulose, dextrates, kaolin, mannitol, silicic acid, sorbitol, pre-gelatinized starch, glycine, and mixtures thereof.

In particular embodiments, the filler is dextrin, maltodextrin, or a mixture thereof. In a particularly preferred embodiment, the filler comprises or consists of maltodextrin.

The extract may be combined with the filler(s) (e.g. maltodextrin, or dextrin and maltodextrin) at one or more points in the process (e.g. at the start of during the concentration step; after the concentrating step to the syrupy paste obtained thereby; during the drying process; after the drying step to the dryish paste obtained thereby; before, during or after bulk product formation (e.g. before bulk granule formation); during the preparation of a dosage form which may be a unit a dosage form such as a capsule or tablet). Accordingly, the extract may be combined with the filler(s) when the extract is in various forms or stages of processing, such as to the extract product of the concentration step, or to the extract product of the drying step. The extract may be combined with the filler(s) when the extract is in the form of the syrupy paste of the invention, the dryish paste of the invention, a lumpy mixture of the invention, or bulk product of the invention etc.

In certain embodiments, the filler(s) if present, is combined with the product of the drying step. The resulting mixture of extract and filler(s) may then conveniently be made into bulk product such as bulk granules.

When the filler(s) is combined with the extract the mixture may be homogenized, e.g. by use of a mixer. Use of a mixer may also enable the size of lumps formed by the filler and extract mixture to be reduced.

The amount of filler combined with the extract may be adjusted for the 'stickiness' of the extract. In particular, where the extract is very sticky (e.g. as in the case of the syrupy paste obtained by the solvent removal/concentrating step) higher amounts of filler may be desirable. A mixer, such as a high shear mixer, may optionally be used to facilitate the mixing of the filler and the extract particularly when the extract has a high degree of 'stickiness'.

Typically, however, the extract may be combined with filler (e.g. maltodextrin) to produce a composition wherein the filler is: about 10% to about 30% of the combined weight of the filler and extract; preferably about 15% to about 25% of the combined weight of the filler and extract; more preferably about 18% to about 22% of the combined weight of the filler and extract; and yet more preferably about 20% of the combined weight of the filler and extract. To achieve such amounts, the filler may be combined with the extract at one or more (e.g. two, three or four) stages of the process.

In certain embodiments, filler is combined with the extract after it has been subjected to a drying step. In a particular embodiment, filler is combined with the extract after it has been subjected to a drying step and prior to the formation of bulk product such as bulk granules. After addition to the extract, the filler may, for example, represent about 10% to about 30%, about 15% to about 25%, about 18% to about 22%, or about 20% of the combined weight of the filler and extract. As described below, the mixture of filler and extract may then be optionally processed into bulk product, such as bulk granules (e.g. by grinding and sieving).

In certain embodiments, the one or more fillers is combined with the extract at two or more stages of the process. For example, the filler(s) may be combined with the extract after it has been subjected to a drying step (e.g. to the dryish paste of the invention) with further filler then being combined with the extract when the extract has been processed into granules such as by grinding and sieving. The latter may optionally be during dosage formation, such as during the filling of capsules with the extract or during tableting. In this way, the one or more fillers (e.g. maltodextrin) may be divided into two or more portions to be added to the extract at two or more stages in the post-extraction processing of the extract, preferably resulting in product where the weight of filler is about 10% to about 30%, about 15% to about 25%, about 18% to about 22%, or about 20% of the combined weight of the filler and extract.

In certain embodiments, the extract of the invention is provided in the form of bulk product. Bulk product is typically intended or designed for filling or forming into unit dosage forms, such as for filling into capsules or for forming into tablets. Accordingly, in certain embodiments bulk product of the invention is used for filling or forming into unit dosage forms. Similarly, in certain embodiments the unit dosage forms of the invention may be prepared by filling or forming bulk product of the invention into said unit dosage forms.

Optionally the bulk product comprises, in addition to the extract of the invention, one or more further moieties, such as one or more excipients. Optionally said one or more excipients includes a filler and may further include a lubricant and/or glidant.

In certain embodiments, the bulk product is bulk granules. In a particular embodiment, a mixture comprising extract and filler (e.g. maltodextrin) as described above is used to prepare the bulk granules. Optionally, the preparation of bulk granules from the extract/filler mixture of the invention (which for the avoidance of doubt may optionally comprise one or more further ingredients, such as one or more further excipients and/or one or more further active ingredients) comprises preparing granules of a desired and/or homogenized size from the extract/filler mixture. Suitable methods will be known to those skilled in the art, but in one embodiment this may be comprise grinding and sieving the extract/filler mixture. The resultant granules may optionally undergo a drying step, e.g. by using a drier such as a fluid-bed drier or shelf drier. In other embodiments such a drying step is omitted, such as where drying is deemed unnecessary or where adequate drying of the granules may have been achieved during the process of forming the granules. For instance, where grinding is used, heat created during the grinding process will encourage evaporation of any residual solvent.

In certain embodiments of the invention, the bulk product of the invention may comprise one or more lubricants. Accordingly, the preparation of the bulk product of the invention may comprise adding one or more lubricants to the bulk product. Non-limiting examples of lubricants include: metallic stearates (such as magnesium stearate, calcium stearate, or aluminium stearate), talc, hydrogenated castor oil, sodium stearyl fumarate, sucrose esters of fatty acids, waxes, hydrogenated vegetable oils, sucrose fatty acid esters, polyethylene glycol, light anhydrous silicic acid, dried aluminium hydroxide gel, stearic acid, synthetic aluminium silicate and magnesium silicate. If present, the one or more lubricants may conveniently comprise or consist of one or more metallic stearates, e.g. magnesium stearate and/or calcium stearate. In certain embodiments the one or more lubricants is maltodextrin.

Additionally, as discussed above, in certain embodiments Acori oil may be added to the bulk product of the invention, such as during the process of mixing bulk granules with lubricant. In other embodiments, the Acori oil is not used in the preparation of the products of the invention and is therefore by-product or waste product which can be discarded.

In certain embodiments of the process described herein, one or more biomarkers may be analysed. Biomarkers may, for example, be analysed in one or more of: the raw material (i.e. the herbs) to provide a means of quality control for the raw material; the extraction medium (e.g. to monitor the progress of extraction or to determine a suitable extraction process endpoint); an extract of the process, such as the extraction solution obtained by the extraction step (e.g. after cooling of the extraction solution and/or separation of non-soluble solids from the same); the extract obtained following the solvent removal step (which in at least some embodiments is in the form of a syrupy paste); the extract obtained following a drying step (which in at least some embodiments is in the form of a dryish paste); and/or the bulk product of the invention (e.g. bulk granules); or any other herbal product of the invention. Analysis of the raw material, the extract obtained following the drying step (e.g. in the form of a dryish paste), or bulk product (e.g. bulk granules) may be preferred.

The analysis of particular biomarkers may comprise qualitative and/or quantitative measurement of the biomarker. The methodology used may be any suitable method known in the art, and includes any method accepted or developed by one of skill in the art for the particular biomarker being analysed. Examples of methods of analysis include HPLC and GC. In Table 2 below, HPLC is conveniently used, except GC may be used to analyse the volatile oil from the herb *Rhizoma Acori tatarinowii*.

In one embodiment, analysis is performed on one or more biomarkers (e.g. one) for each herb used. The biomarker(s) are preferably unique to that particular herb. Biomarkers suggested by official books (e.g. Pharmacopoeias) or otherwise available in the literature may optionally be used. In certain embodiments, the biomarker(s) represent a major ingredient of the herb and/or are at least in part responsible for the bioactivity of the herb.

TABLE 2

The MLC901 herbs and corresponding biomarkers

| Herb | Biomarkers (per Chinese Pharmacopoeia) | Other proposed Biomarkers |
|---|---|---|
| *Radix Astragali* | Astragaloside IVCalycosin; 7-O-b-D-glycoside | |
| *Rhizoma Chuanxiong* | Ferulic acid | Z-Butyliedenephthalide; Tetramethylpyrazine |
| *Radix Angelicae sinesis* | Ferulic acid | Z-Liguistilide |
| *Radix Paeoniae rubra* | Paeoniflorin | |
| *Radix Polygalae* | Tenuifolin; Polygalaranthrone III; 3,6'disinapolysucrose | |
| *Radix Salvia miltiorrhizae* | Tanshinone II; Salvianolic acid B | |
| *Carthamus tinctorius* | Hydroxy safflower Yellow A; Kaempferol | |
| *Semen Persicae* | Amygdalin | |
| *Rhizoma Acori tatarinowii* | Total volatile oil | |

The extracts, compositions and other herbal products produced according to the present invention can be used in a wide variety of useful applications.

In certain embodiments, the herbal extract or herbal product is selected from the group consisting of:
1. an extract obtained or obtainable by a process of the invention;
2. a composition comprising an extract obtained or obtainable by a process of the invention, wherein the composition optionally comprises at least one carrier, diluent or excipient; and
3. a composition comprising an extract obtained or obtainable by a process of the invention, wherein the composition is a therapeutic and/or prophylactic herbal composition, a pharmaceutical composition, nutraceutical or phytoceutical.

Accordingly, an extract of the invention may optionally be formulated as a therapeutic and/or prophylactic herbal composition, a pharmaceutical composition, nutraceutical or phytoceutical. In certain embodiments, a composition of the invention may be formulated into a unit dosage form, such as a dosage form for oral administration.

In addition to the extract of the invention, the herbal products or compositions of the invention may further comprise one or more further active ingredients.

A pharmaceutical composition of the invention may comprise an extract of the invention and at least one pharmaceutically acceptable carrier, diluent or excipient. Suitable examples of carriers, diluent and excipients are discussed elsewhere herein. In a particular embodiment, the pharmaceutical composition comprises at least one diluent (e.g. maltodextrin) and optionally further a lubricant (e.g. magnesium stearate) and/or glidant.

As used herein, the term "pharmaceutical composition" includes a reference to the combination of an extract of the invention with a pharmaceutically acceptable carrier, diluent or excipient. The pharmaceutical compositions of the invention will typically be for use as a prophylactic or therapeutic pharmaceutical composition for in vivo human use.

The phytoceuticals of the invention may, in addition to comprising the extract of the invention, optionally comprise other plant-derived components. The phytoceuticals can be delivered by such non-limiting vehicles as teas, tonics, juices or syrups.

The nutraceuticals contemplated by the present invention may provide nutritional and/or supplemental benefits and therefore be delivered, for example as a food or beverage product, dietary supplement, extract, or the like. The term "dietary supplement" as used herein includes a reference to a preparation or formulation which is added to or otherwise included in a subject's normal diet, and is therefore present in addition to the normal diet.

The present invention provides extracts and other herbal products obtained or produced (the terms 'obtained' and 'produced' may be used interchangeably) by a process of the present invention. The extract may be the extract as produced or as processed at any stage of the processes of the invention. As will be appreciated from the discussion herein, the extract as produced by the extraction step of the process may undergo various further processing steps such as separation from particulate matter, concentrating, drying, granulation, etc. and such forms of the extract form part of the present invention.

The term 'extract' as used herein is intended to be interpreted broadly and includes a reference to any substance, such as a composition, which comprises or consists of the TCM extract(s) as present in the liquid extraction solution as produced by the extraction step(s) of the invention. It should be appreciated that the term "extract" can be used to refer to the extract when in solid or liquid form.

The extract of the present invention may optionally be in the form of:
1. The extraction liquid, i.e. the liquid solution present at the end of the extraction process of the present invention. The extraction liquid may optionally have been separated from the particulate matter present at the end of the extraction process.
2. The concentrated extract as produced by the concentration (solvent recovery) step—this extract may be in the form of a syrupy paste
3. The dried extract as produced by the drying step. As discussed herein, the extract typically retains some moisture from the solvent and so it may be more correctly referred to as a 'dryish' extract, but for convenience the two terms may be used interchangeably. The dried extract may be in the form of a dryish paste.
4. The dried extract combined with one or more excipients, such as maltodextrin.
5. Bulk product e.g. bulk granules.
6. The bulk product (e.g. bulk granules) combined with one or more lubricants (e.g. Mg stearate) and/or glidants.
7. A therapeutic and/or prophylactic herbal composition, a pharmaceutical composition, nutraceutical or phytoceutical.
8. Any of the above comprising one or more further ingredients As indicated in the list above, the extracts of the invention may be combined with one or more further ingredients. Examples of the additional further ingredient(s) which may be combined with an extract of the invention (whether in the form of a solution of the extract, a syrupy or dryish paste of the extract, granules of the extract etc.) include, but are not limited to, the following: one or more further active ingredients (e.g. pharmaceutical compounds or compositions, other therapeutic agents; traditional medicine (e.g. TCM or Kampo medicine) etc.), fillers; other herbs/herbal extracts/herbal material; TCM ingredients; preservatives; pharmaceutically acceptable additives, carriers, fillers (diluents), or excipients; and mixtures of two or more of the foregoing.

Also envisaged within the scope of the invention are other forms or compositions comprising an extract of the invention, which may be produced by further processing of the extract. For example, in one embodiment the extract may be processed into 'bulk' or 'stock' product which may optionally be bulk granules, bulk powder, bulk beads, bulk beadlets, and/or bulk pellets. Thus, in some embodiments the herbal extract or herbal product may be bulk product comprising the extract of the invention. The bulk product of the invention may be used for loading in capsules or forming into tablets or for producing other dosage forms. The stock granulation product of the invention may conveniently be formulated or further processed to produce a therapeutic and/or prophylactic herbal composition, a pharmaceutical composition, nutraceutical or phytoceutical of the invention.

The herbal extracts and herbal products of the invention can be in a solid or liquid form. Semi-solid or semi-liquid compositions are also envisaged.

The form of the herbal extract or herbal product may vary according to the intended use or purpose of the same (e.g. as a pharmaceutical composition or dietary supplement), as well as the manner of its intended use (e.g. the route of administration). Non-limiting examples of product forms of the herbal extracts and herbal products of the invention may include: capsules, caplets, tablets, beads, granules, solutions or suspensions in aqueous or non-aqueous liquids, freeze-dried products, powder, pastes, emulsions, troches, lozenges, dispersible powders or granules, syrups, elixirs, oil-in-water liquid emulsions, water-in-oil liquid emulsions or any combination thereof. Preferably, the herbal extracts or herbal products of the invention are formulated as capsules, caplets, tablets, beads, or granules; capsules and granules are particularly preferred.

In certain embodiments, the herbal extract or herbal product of the invention is in the form of granules, powder, beads, pellets or the like for loading in capsules, forming into tablets or for preparing one or more other dosage forms which are preferably unit dosage forms.

Such granules, powder, beads, pellets or the like which may be regarded as an intermediate product or precursor to the final formulation/dosage form as provided to the end-user (e.g. patient), are termed herein as 'bulk granules', 'bulk powder', 'bulk beads' and 'bulk pellets'. Such intermediate products may be referred to collectively as 'bulk product'. Preferably, such bulk product is for loading in capsules, and preferably the bulk product is bulk granules. Alternatively such bulk product, whether in the form of 'bulk granules', 'bulk powder, 'bulk beads' and 'bulk pellets' or the like, may be used for forming tablets e.g. by compression or molding.

In certain embodiments, pharmaceutical compositions are provided which may preferably be in the form of capsules or tablets formulation and/or preferably for oral use. Suitably the pharmaceutical compositions of the invention comprise an extract of the invention and one or more pharmaceutically acceptable carriers, diluents or excipients.

The dosage forms, unit dosage forms and formulations of the invention (e.g. therapeutic and/or prophylactic herbal compositions, pharmaceutical compositions, neutraceuticals, phytoceuticals) may be prepared or formulated by any suitable method and may include using conventional pharmaceutical compounding techniques. The term 'formulating' as used herein is intended to be interpreted broadly and includes a reference to any suitable process (or processes) for preparing a herbal extract or herbal product of the invention in a form suitable for administration to a subject, e.g. a human. The term 'formulating' may be used interchangeably with term 'preparing'.

Methods for the production of capsules are well known in the art. In certain embodiments, capsules may be formed by loading the capsules with bulk granules or other bulk product.

Methods for forming tablets are well known in the art and may, for example, include preparation by compression or molding. Tablets may optionally be prepared using bulk product (e.g. bulk granules or bulk beads).

Optionally, the tablets and/or capsules of the invention can include an outer protective coating which comprises a coating polymer, such as, for example, polyvinyl alcohol (PVA), hydroxypropyl methyl cellulose, and hydroxypropyl cellulose, and/or a plasticizer(s) and optional colorant(s). Other optional components of the outer protective coating include anti-adherent(s) and/or (s) and opacifying agent(s).

In certain embodiments, the herbal extract or herbal product of the invention is a liquid formulation. A liquid formulation may, for example, be prepared by combining the extract with a suitable liquid to form a liquid embodiment of the present invention. A suitable liquid may, for example, be an aqueous liquid (e.g. water or other suitable liquid such as a dilute acid solution or flavoured aqueous solution) or a non-aqueous liquid. In one embodiment, the liquid may be a non-toxic alcoholic vehicle. As with the other formulations of the invention, the liquid formulations of the invention may comprise one or more excipients in addition to the extract of the invention.

Liquid formulations for oral administration are particularly preferred. Non-limiting examples of excipients used in oral fluids for oral administration include, but are not limited to, solubilizers, emulsifiers, flavoring agents, preservatives, and coloring agents.

The herbal extracts or herbal products of the present invention may be for administration singly or in combination with one or more additional active ingredients or therapeutic agents. Where any of the herbal extracts or products of the invention are used in combination with one or more additional active ingredients or therapeutic agents, each of the components of the combination can be administered simultaneously or sequentially and in any order, and the components can be administered separately or as a fixed combination. The one or more additional active ingredients or therapeutic agents may optionally be in the same dosage form as the herbal extract or herbal product of the invention or in a separate dosage form.

The herbal extracts or herbal products of the present invention may be administered by any suitable route, such as orally, parenterally, intravenously, subcutaneously, intradermally, intraperitoneally or topically, in liquid, semi-liquid or solid form. Accordingly herbal extracts and herbal products formulated for the aforementioned routes of administration are contemplated and form part of the present invention.

In a preferred embodiment, there is provided a herbal extract or herbal product according to the present invention wherein the herbal extract or herbal product is adapted for oral administration, preferably for oral administration to a human. The herbal extracts and herbal products for oral administration may be formulated in any known or otherwise suitable product form for oral administration. Preferably, the herbal extracts and herbal products for oral administration are in a unit dosage form for administration orally, such as in the form of capsules, or tablets. Capsules are particularly preferred.

The dosage of the herbal extracts and herbal products described herein (e.g. pharmaceutical, therapeutic or herbal compositions) to be administered is not subject to defined limits, but will usually be an effective amount. The quantity for providing an effective amount may be contained in one or a plurality of individual dosage forms, e.g., in one capsule or a plurality of capsules.

The terms "effective amount" or "therapeutically effective amount," as used herein, include a reference to a sufficient amount being administered which will treat prophylactically or therapeutically to some extent, such as to a clinically significant extent, one or more of the signs, symptoms or causes of the disease or disorder being treated. The term also includes within its scope amounts effective to enhance normal physiological function or to achieve any other desired alteration of a biological system. An appropriate "effective" amount in any individual case may be determined through standard empirical methods which are well known in the art, such as a dose escalation study.

MLC901 is typically administered orally, twice daily (BID) with three 0.4 g capsules being administered each time. Hence, a daily dose of about 2.4 g is envisaged. The duration of treatment is typically 3 months which represents 3 courses of treatment, adaptable with regard to the patient's condition. This dosage is suitable for stroke treatment. For other diseases, the treatment can last longer. For patients with swallowing difficulties, capsules may be opened and powder diluted in water that can be drunk as such or injected via a gastric tube.

TABLE 3

Weight of MLC901 components (as dried herbs) used in one embodiment of the present extraction process

| MLC901 components | Weight (mg) to produce approx. 300 mg extract |
| --- | --- |
| *Radix astragali* | 800 |
| *Radix salviae miltiorrhizae* | 160 |
| *Radix paeoniae rubra* | 160 |
| *Rhizoma chuanxiong* | 160 |
| *Radix Angelicae sinensis* | 160 |
| *Carthamus tinctorius* | 160 |
| *Semen persica* | 160 |
| *Radix polygalae* | 160 |
| *Rhizoma acori tatarinowii* | 160 |

The extract produced from the ingredients in Table 3 above may be combined with dextrin (57 mg), maltodextrin (51 mg or 61 mg) and magnesium stearate (2 mg) and filled into number zero capsules.

If the bulk product (e.g. bulk granules) is stored, transported, packaged for sale or the like, then it is suitably kept under conditions to discourage or minimize the absorption of water by the granules and/or which discourages or minimizes any other unwanted change or deterioration in the product. Suitable conditions for containing the granules will be apparent to those skilled in the art. Preferably the granules are kept under hermetically sealed conditions in a material which is impermeable to water vapor and air, or which allows only minimal permeation by water vapor and air. The granules may be protected by a desiccant, for example by way of sachets or other suitable containers of desiccant. In addition, the granules may be packaged with instructions for use and/or some other form of information regarding the product.

In certain embodiments, a herbal extract or herbal product of the invention, such as a pharmaceutical composition, formulation or dosage form (e.g tablets, capsules or caplets), is contained under conditions to discourage or minimize the absorption of water by the product and/or which discourages or minimizes any other unwanted change or deterioration in the product. Suitable conditions will be apparent to those skilled in the art. Preferably, the product is contained under hermetically sealed conditions in a material which is impermeable to water vapor and air, or which allows only minimal permeation by water vapor and air. Optionally the product may be protected by a desiccant, for example by way of sachets or other suitable containers of desiccant.

In one embodiment, suitable conditions may comprise where the product is contained within a blister pack. Preferably, the blister pack is made of a material that allows only minimal permeation by water vapor and oxygen. In one embodiment the blister pack is comprised of a metal foil. The blister pack may be further protected by storing in an aluminium container such as an aluminium sachet or bag.

In another embodiment, suitable conditions may comprise storing the product in a bottle which has low or minimal impermeability to oxygen and water vapour. In one embodiment, the bottle further comprises a desiccant. In one embodiment, the bottle further comprises an oxygen scavenger or molecular sieve.

In certain embodiments, the products of the invention may be packaged with instructions for use and/or some other form of information regarding the product.

The herbal extracts and herbal products of the present invention (e.g. pharmaceutical compositions) are not limited to only those for humans but also include those for various animals, in particular, other mammals. Healthy individuals may be administered a herbal extract or herbal product of the present invention (e.g. as a dietary or health supplement), as well as individuals suffering from a disease or disorder for which the herbal extracts or herbal products of the present invention may provide prophylactic or therapeutic benefit as well as individuals predisposed to or at risk of such a disease or disorder.

As discussed above, various uses have been described in the art for certain known products which include herbal extracts prepared according to this invention (e.g. MLC601 and MLC901; NeuroAiD™ and NeuroAiD II™). It is envisaged that the herbal extracts and herbal products prepared by the extraction process of this invention may be similarly used to treat conditions described for MLC601, MLC901 and the like in WO2007/106049, WO2010/053456, WO2010/110755 and WO2013141818, the contents of which are incorporated in their entirety.

The herbal extracts and herbal products of the present invention may find particular utility in treating (therapeutically or prophylactically) individuals who are suffering from, or who are predisposed to or at risk from a disease or disorder selected from the group consisting of: stroke, cerebral stroke which may be ischemic or haemorrhagic cerebral stroke, myocardial infarction, neurological disorders, neurodegenerative disorders including Alzheimer's and Parkinson's, conditions related to neuroplasticity, psychiatric indications (e.g. anxiety disorders, schizophrenia, depression, and post-natal depression), epilepsy, seizures, demyelinating diseases (for example, multiple sclerosis), cerebral palsy, traumatic injuries to or tumours in the brain, spinal cord or peripheral nerves, dementia, obesity, incontinence (e.g. urinary incontinence), hypertension, ischemic or reperfusion injury; diseases or disorders benefiting from neuroprotection; and diseases or disorders benefiting from neuroconditioning.

The herbal extracts and herbal products of the present invention have improved consistency in terms of chemical composition and/or biological activity. Biomarkers, including those described herein, can provide a useful measure of such product consistency and/or biological activity. Assays and animal models can also provide a means for verifying biological activity. Suitable assays may include assays for the neurobiological properties of the products of the invention, such as their ability to reduce infarct volume after ischaemia, and to reduce neurological deficits after stroke. One suitable animal model is described in the Examples Section hereinafter.

As discussed above, the process of the present invention does not require multiple extractions on the same mass. By avoiding multiple extractions on the same mass this may not only provide certain advantages in terms of procedural efficiency and potential cost savings arising from reduced energy or solvent consumption, but can also confer certain advantages on the resulting products. Specifically, multiple extractions on the same material is likely to result in undesired plant material (e.g. starch, sugars, proteins and lipids) in the extract, thereby adding unwanted bulk to the product without any additional therapeutic value to the product. The products of this invention may also benefit from increased potency due to the reduced amount of unwanted material present.

The extracts/products of the present invention can also differ in chemical composition from known products and extracts due to the extraction process conditions used. Thus, the conditions used herein to extract the TCM herbs may result in different moieties being extracted, or moieties being extracted in a more favourable concentration to elicit desired biological activity, than in earlier, known, extraction processes. In view of the foregoing it will be appreciated that the extracts/products of the invention may possess beneficial and novel properties, including one or more of the following:

i. a superior level of one or more biomarkers for one or more of the herbs used. In certain embodiments, the one or more biomarkers may comprise one or more of the biomarkers set forth in Table 2 above, or be selected from the biomarkers set forth in Table 2;
  ii. a reduced level of undesired or inactive extracted plant material. Such undesired plant material may comprise, for example, starch, sugars, proteins and lipids; and/or
  iii. increased potency.

One aspect of the invention provides a herbal extract or herbal product, prepared by a process which comprises heating a mixture of the following herbs:
  (i) *Radix Astragali* (root of Membranous Milkvetch or Huang Qi);
  (ii) Rhizome of *Ligusticum Chuanxiong* (Chuan Xiong);
  (iii) *Radix Angelicae sinensis* (root of Chinese *Angelica* or DanGui); and
  (iv) *Radix Polygalae* (root of thinleaf milkwort, *Polygala tenuifolia* Willd., *Polygala sibirica* L. or Yuanzhi); in an aqueous organic solvent.

Another aspect of the invention provides a new herbal extract or product having an increased level of one or more biomarkers in one or more of the extracts of the herbs (i), (ii), (iii) and (iv) above, relative to known products derived from herbs including (1), (ii), (iii) and (iv) above, such as MLC601 and/or MLC901. In a particular aspect, the herbal extract or product has an increased level of one or more of the biomarkers described in Table 2 above.

Another aspect of the invention provides a new herbal extract or product having a reduced level of undesired or inactive extracted plant material, relative to known products derived from herbs including (i), (ii), (iii) and (iv) above, such as MLC601 and/or MLC901.

Another aspect of the invention provides a new herbal extract or product having increased potency relative to known products derived from herbs including (i), (ii), (iii) and (iv) above, such as MLC601 and/or MLC901.

The novel herbal extracts and herbal products of the invention comprise extracts of at least (i), (ii), (iii) and (iv) above, and may optionally also comprise extracts of one or more (i.e. 1, 2, 3, 4 or 5) of the following herbs:
  a) *Radix et Rhizoma Salviae Miltiorrhizae* (Red Sage root or Dan Shen);
  b) *Radix Paeoniae rubra* (Red Peony root):
  c) Flower of *Carthamus Tinctorius* (Safflower or HongHua);
  d) *Semen Persicae* (*Prunus Persica* seeds or Taoren); and
  e) *Rhizoma Acori tatarinowii* (rhizome of grassleaf sweetflag or Shichangpu).

In certain embodiments, the novel herbal extracts and herbal products of this invention comprise extracts derived from the nine herbs (i), (ii), (iii) and (iv) and a), b), c), d) and e) above.

The novel herbal extracts and herbal products of this invention are prepared according to the extraction process of this invention, followed where appropriate, by subsequent processing steps, including:
  i. separating particulate matter from the extraction solution;
  ii. concentrating the extraction mixture by removing the solvent; and
  iii. drying the concentrated extraction mixture to yield a dried extraction product.

In certain embodiments, volatile oil from *Radix Angelicae sinensis* and/or *Chuanxiong* may conveniently be added to the herbal extract or herbal product. Similarly, the process of the invention for preparing herbal extracts or herbal products may optionally comprise the step of removing volatile oil from the *Radix Angelicae sinensis* and/or *Chuanxiong* and adding the removed oil to the subsequent herbal extract or herbal product.

In order that the invention may be readily understood and put into practical effect, particular embodiments are described in the following, non-limiting, examples.

Example 1

Active Materials:

| | Name | Part used | Quantity/batch |
|---|---|---|---|
| 1 | *Astragali membranaceous Radix* | Dried roots | 275 g |
| 2 | *Salvia miltiorrhiza Radix* | Dried roots & rhizomes | 55 g |
| 3 | *Paeoniae rubra Radix* | Dried roots | 55 g |
| 4 | *Chuanxiong* (*Ligusticum chuanxiong*) *Rhizoma* | Dried stem/rhizome | 55 g |
| 5 | *Radix Angelicae sinensis* | Dried roots | 55 g |
| 6 | *Carthami* (*Carthamus tinctorius*) *Flos* | Dried flower | 55 g |
| 7 | *Persicae* (*Prunus persica*) *Semen* | Dried ripe seeds | 55 g |
| 8 | *Polygalae* (*P. Tenuifolia*) *Radix* | Dried roots | 55 g |
| 9 | *Acori tatarinowii Rhizoma* | Dried stem/rhizome | 55 g |
| | Total | | 715 g |

Step 1: Each raw material (except *Flos carthami*) was individually powdered in a pulveriser to a sieve mesh size of about number 8 to 10. To minimise heat generated during pulverization, a jacketed pulverizer through which cold water can be circulated may be used.

Step 2: Each powdered material was weighed as per the quantity mentioned in the table above.

Step 3: *Flos carthami* was powdered in a domestic electrical mixer along with *Chuanxiong* and *Angelica* which had both been previously powdered individually.

Step 4: 55 g of Aeon; powder was transferred to a round bottom flask of 3 litres, and 50 ml of distilled water added to wet the material to facilitate steam distillation. The Acori was subjected to steam distillation by bubbling steam through the Acori bed, and the steam along with the volatile oil then passed through the condenser to condensate. The process continued until 1100 ml of distillate was collected which took about 4.5-5 hours. Steam was generated separately by heating water in a closed vessel. This step removes beta and alpha asarone present in the volatile oil of Acori.

Step 5: The distillate from Step 4 above was allowed to cool. The Acori along with the decoct remaining in the flask were used in the subsequent extraction step along with the other herbs.

Step 6: The 1100 ml of Acori decoct and the Acori residue was transferred to an extractor and the other eight herbs are added to the extractor as per the quantities mentioned in the above table, followed by 650 ml of distilled water and 4.5 litres of absolute alcohol (99.9%) to obtain a final concentration of alcohol of about 72%. The extractor was a 20 litre stainless steel (316 grade) jacketed extractor fitted with stirrer and condenser. The extractor was jacketed for circulation of water which may be heated with an electric heater to increase the temperature of the reactor contents. The extractor was also fitted with a saw tooth blade stirrer at 100-200 rpm.

Step 7: The reactor heater was switched on and heating of the contents started while stirring (stirrer at 200 rpm). It took about 15 minutes to reach the temperature of 65-70° C. Thereafter, the extraction continued for 3 hours with the temperature maintained at 65-70° C.

Step 8: The resultant extract was filtered through a basket centrifuge with 20 micron PP filter bag. The yield of extract was 5.060 litres and the time required was 15 min.

Step 9: The hydro-alcoholic solvent was then removed with the resultant extract concentrated under reduced pressure (3-5 psi or 0.207-0.345 bar) at 60-70° C. temperature to a syrupy consistency. The yield of paste is about 250 g.

Step 10: The pasty mass of extract was then dried using a microwave oven to yield a dry paste (about 180 g to 190 g).

Step 11: The dry paste was then mixed with 20% maltodextrin and powdered in a mixer and dispensed into 5 g vials.

Example 2A

Active Materials:

| | Name | Part used | Quantity/batch |
|---|---|---|---|
| 1 | *Astragali membranaceous Radix* | Dried roots | 315 g |
| 2 | *Chuanxiong (Ligusticum chuanxiong) Rhizoma* | Dried stem/rhizome | 63 g |
| 3 | *Radix Angelicae sinensis* | Dried roots | 63 g |
| 4 | *Polygalae (P. Tenuifolia) Radix* | Dried roots | 63 g |
| | | Total | 504 g |

Step 1: Each raw material was individually powdered in a pulveriser to a sieve mesh size of about number 8 to 10. To minimise heat generated during pulverization, a jacketed pulverizer through which cold water can be circulated may be used.

Step 2: Each powdered material was weighed as per the quantity mentioned in the table above.

Step 3: *Chuanxiong* and *Angelica*, which had both been previously powdered individually, were transferred to a round bottom flask of 3 litres, and 250 ml of distilled water added to wet the material to facilitate steam distillation. The wet material was subjected to steam distillation by bubbling steam through the bed, and the steam along with the volatile oil then passed through the condenser to condensate. The process continued until about 1000 ml of distillate was collected which took about 4 hours. Steam was generated separately by heating water in a closed vessel. The volatile oil removed by this distillation step was discarded.

Step 4: The distillate from Step 3 above, together with condensed steam, was allowed to cool yielding 1400 ml of extract.

Step 5: The 1400 ml of extract was transferred to an extractor and the other two herbs are added to the extractor as per the quantities mentioned in the above table, followed by 2.8 litres of absolute alcohol (99.9%) to obtain a final concentration of alcohol of about 66.6%. The extractor was a 20 litre stainless steel (316 grade) jacketed extractor fitted with stirrer and condenser. The extractor was jacketed for circulation of water which may be heated with an electric heater to increase the temperature of the reactor contents. The extractor was also fitted with a saw tooth blade stirrer at 100-200 rpm.

Step 6: The reactor heater was switched on and heating of the contents started while stirring (stirrer at 200 rpm). It took about 15 minutes to reach the temperature of 65-70° C. Thereafter, the extraction continued for 3 hours with the temperature maintained at 65-70° C.

Step 7: The resultant extract was filtered through a basket centrifuge with 20 micron PP filter bag. The yield of extract was 3.080 litres and the time required was 15 min.

Step 8: The hydro-alcoholic solvent was then removed with the resultant extract concentrated under reduced pressure (3-5 psi or 0.207-0.345 bar) at 70° C. temperature to a syrupy consistency. The yield of paste is about 225 g.

Step 9: The pasty mass of extract was then dried using a microwave oven to yield a dry paste (about 140 g to 150 g).

Step 11: The dry paste was then mixed with 20% maltodextrin and powdered in a mixer and dispensed into 5 g vials.

Example 2B

Product was also produced in a similar manner to Example 2A, except Steps 3 and 4 were eliminated and all four powdered herbs were added to the extractor as per the quantities mentioned in the above table. In this example, the extraction used 66.66% absolute alcohol and 33.33% water.

Example 2C

Product was also produced in a similar manner to Example 2A, except Steps 3 and 4 were eliminated and all four powdered herbs were added to the extractor as per the quantities mentioned in the above table. In this example, the extraction used 80% absolute alcohol and 20% water.

Example 2D

Product was also produced in a similar manner to Example 2A, except Steps 3 and 4 were eliminated and all four powdered herbs were added to the extractor as per the quantities mentioned in the above table. In this example, the extraction used 40% absolute alcohol and 60% water.

Example 2E

Product was also produced in a similar manner to Example 2A, except Steps 3 and 4 were eliminated and all four powdered herbs were added to the extractor as per the quantities mentioned in the above table. In this example, the extraction used a mixture of isopropyl alcohol and water as solvent in a ratio of 70:30.

Example 2F

Product was also produced in a similar manner to Example 2A, except Steps 3 and 4 were eliminated and all four powdered herbs were added to the extractor as per the quantities mentioned in the above table, In this example, the extraction used a mixture of ethanol, isopropyl alcohol and water as solvent in a ratio of 40:30:30.

In certain embodiments, when scaling up this process, a high shear mixer with a blunt blade may be used for mixing the paste with maltodextrin (or other filler, if used) and homogenizing the mixture. A grinder and sieve may then be used to produce granules of similar size.

Example 3—Animal Model

SD male rats (240 g to 280 g) were subjected to a focal cerebral ischaemia test using a generally known procedure of middle cerebral artery occlusion (MCAo). In the test, the internal carotid artery of each rat was occluded using a commercial monofilament whilst the left common carotid artery and left external carotid artery were isolated and ligated. The right common carotid artery was then ligated. After 50 minutes the right common carotid artery was released, and the monofilament removed 10 minutes later along with the release of the left common carotid artery to allow reperfusion.

The test product, as a saline solution, and vehicle (saline) were given to the rats via intraperitoneal injection 30 minutes after reperfusion. The animals were sacrificed after 24 hours post-reperfusion, their brains isolated and brain slices analysed for infarct volumes. The percentage of infarct area was calculated as follows:

Contralateral hemisphere area−(ipsilateral hemisphere area−infarct area)/contralateral hemisphere area×100%.

Example 4—Results

A. Using the process of Example 1 four lab scale batches of product were tested in the neurological animal model (see Example 3 above). Infarct volume results are as described in the table below:

| Batch | Example 1 Product | Vehicle | SEM* Product | SEM** Vehicle |
|---|---|---|---|---|
| 1 | 32.91 | 48.22 | 4.72 | 4.65 |
| 2 | 23.9 | 40.01 | 3.77 | 8.4 |
| 3 | 32.57 | 45.5 | 6.4 | 4.47 |
| 4 | 25.14 | 42.41 | 4.79 | 2.99 |

*Standard error of the mean of results for the product of Example 1
**Standard error of the mean of results for vehicle B. Using the process of Example 2 lab scale batches of product were tested in the neurological animal model (see Example 3 above). Infarct volume results for the product of Example 2C are as described in the table below:

| Example | Example 2 Product | Vehicle | SEM* Product | SEM** Vehicle |
|---|---|---|---|---|
| 2C | 22.64 | 44.91 | 4.48 | 6.65 |
| 2F | 31.32 | 46.80 | 3.55 | 4.89 |

*Standard error of the mean of results for the product of Examples 2C and 2F
**Standard error of the mean of results for vehicle

The invention claimed is:

1. A process for preparing a mixture of herbal extracts consisting of:
   (i) *Radix Astragali;*
   (ii) Rhizome of *Ligusticum Chuanxiong;*
   (iii) *Radix Angelicae sinensis*; and
   (iv) *Radix Polygalae*
wherein the process comprises heating the herbs in an aqueous organic solvent, to produce a solution containing the herbal extract mixture.

2. A process according to claim 1, wherein the aqueous organic solvent is a hydro-alcoholic solvent.

3. A process according to claim 2 wherein the alcohol in the hydro-alcoholic solvent is ethanol.

4. A process according to claim 2, wherein the alcohol concentration of the extraction mixture is in the range of about 69% v/v to about 75% v/v.

5. A process according to claim 2, wherein the alcohol concentration of the extraction mixture is about 72% v/v.

6. A process according to claim 1, wherein one or more herbs among (i) to (iv) are added to an extractor as dried herbs.

7. A process according to claim 1, wherein the extraction mixture is heated and maintained at a temperature in the range of about 50° C. to about 90° C.

8. A process according to claim 1, wherein the extraction mixture is heated and the elevated temperature maintained for about 60 minutes to about 240 minutes.

9. A process according to claim 1, comprising one or more subsequent steps including a step of separating particulate matter from the extraction solution.

10. A process according to claim 1, comprising one or more subsequent steps including a step of concentrating the extract to yield concentrated extract.

11. A process according to claim 1, comprising one or more subsequent steps including a step of drying the extract to yield dried extract.

12. A process according to claim 1, comprising the following subsequent steps in order:
   (i) separating the particulate matter from the extraction solution by filtration;
   (ii) concentrating the filtrate to yield concentrated extract;
   (3) drying the concentrated extract.

13. A process for preparing a mixture of herbal extracts consisting of:
   (i) *Radix Astragali;*
   (ii) Rhizome of *Ligusticum Chuanxiong;*
   (iii) *Radix Angelicae* sinesis;
   (iv) *Radix Polygae:*
   (v) *Radix et Rhizoma Salviae Miltiorrhizae;*
   (vi) *Radix Paeoniae rubra:*
   (vii) Flower of *Carthamus Tinctorius;*
   (viii) *Semen Persicae*; and
   (ix) *Rhizoma Actori tatannowii* wherein the process comprises heating the herbs in an aqueous organic solvent, to produce a solution containing the herbal extract mixture.

14. A process according to claim 13, followed by mixing the product of the extraction process with TCMs of animal origin: *Buthus Martensii, Eupolyphaga Seu Stelophaga, Calculus Bovis Artifactus, Cornu Saigae Tataricae* and *Hirudo*.

15. A process according to claim 13, wherein one or more herbs among (i) to (ix) are pre-treated to remove a volatile oil, and added to an extractor as a herbal residue and decoct.

16. A process according to claim 13, wherein *Rhizoma acori tatarinowii* is added to the extractor in the form of a residue and decoct of the herb whilst the remaining herbs are added to the extractor as dried herbs.

17. A process according to claim 13, wherein *Rhizoma acori Tatarinowii* is added to the extractor after processing to reduce the level of beta asarone in the *Rhizoma acori Tatarinowii*.

18. A process according to claim 17, wherein the level of beta asarone is reduced by hydro-distillation or steam distillation.

19. A process according to claim 13, wherein the aqueous organic solvent is a hydro-alcoholic solvent.

20. A process according to claim 19 wherein the alcohol in the hydro-alcoholic solvent is ethanol.

21. A process according to claim 19, wherein the alcohol concentration of the extraction mixture is in the range of about 69% v/v to about 75% v/v.

22. A process according to claim 19, wherein the alcohol concentration of the extraction mixture is about 72% v/v.

23. A process according to claim 13, wherein one or more herbs among (i) to (ix) are added to an extractor as dried herbs.

24. A process according to claim 13, wherein the extraction mixture is heated and maintained at a temperature in the range of about 50° C. to about 90° C.

25. A process according to claim 13, wherein the extraction mixture is heated and the elevated temperature maintained for about 60 minutes to about 240 minutes.

26. A process according to claim 13, comprising one or more subsequent steps including a step of separating particulate matter from the extraction solution.

27. A process according to claim 13, comprising one or more subsequent steps including a step of concentrating the extract to yield concentrated extract.

28. A process according to claim 13, comprising one or more subsequent steps including a step of drying the extract to yield dried extract.

29. A process according to claim 13, comprising the following subsequent steps in order:
   (i) separating the particulate matter from the extraction solution by filtration;
   (ii) concentrating the filtrate to yield concentrated extract;
   (3) drying the concentrated extract.

* * * * *